United States Patent
Ozawa

(10) Patent No.: US 10,463,327 B2
(45) Date of Patent: Nov. 5, 2019

(54) X-RAY DIAGNOSTIC APPARATUS, MEDICAL IMAGE DIAGNOSTIC SYSTEM AND CONTROL METHOD

(71) Applicant: Toshiba Medical Systems Corporation, Otawara-shi (JP)

(72) Inventor: Masahiro Ozawa, Sakura (JP)

(73) Assignee: Canon Medical Systems Corporation, Otawara-shi (JP)

( * ) Notice: Subject to any disclaimer, the term of this patent is extended or adjusted under 35 U.S.C. 154(b) by 154 days.

(21) Appl. No.: 15/833,076

(22) Filed: Dec. 6, 2017

(65) Prior Publication Data

US 2018/0168528 A1    Jun. 21, 2018

(30) Foreign Application Priority Data

Dec. 19, 2016  (JP) .................................. 2016-245565
Nov. 14, 2017  (JP) .................................. 2017-219221

(51) Int. Cl.
| | |
|---|---|
| A61B 6/00 | (2006.01) |
| A61B 6/03 | (2006.01) |
| A61B 6/12 | (2006.01) |
| A61B 6/04 | (2006.01) |
| A61B 6/10 | (2006.01) |

(52) U.S. Cl.
CPC ............ *A61B 6/4441* (2013.01); *A61B 6/032* (2013.01); *A61B 6/0407* (2013.01); *A61B 6/0457* (2013.01); *A61B 6/102* (2013.01); *A61B 6/12* (2013.01); *A61B 6/4417* (2013.01); *A61B 6/465* (2013.01); *A61B 6/481* (2013.01); *A61B 6/487* (2013.01); *A61B 6/547* (2013.01); *A61B 6/548* (2013.01); *A61B 6/04* (2013.01);

(Continued)

(58) Field of Classification Search
CPC ..... A61B 6/4441; A61B 6/032; A61B 6/0457; A61B 6/102; A61B 6/12; A61B 6/4417; A61B 6/465; A61B 6/481; A61B 6/487; A61B 6/548; A61B 6/04; A61B 6/4447; A61B 6/504; A61B 6/5205; A61B 6/547; A61B 6/0407
See application file for complete search history.

(56) References Cited

U.S. PATENT DOCUMENTS

2015/0150528 A1* 6/2015 Kim ..................... A61B 6/5205
                                                                378/37
2015/0342557 A1* 12/2015 Kojima ................. A61B 6/102
                                                                378/62

FOREIGN PATENT DOCUMENTS

| JP | 2001-120525 | 5/2001 |
|---|---|---|
| JP | 2008-148866 | 7/2008 |
| JP | 2014-57897 | 4/2014 |

* cited by examiner

*Primary Examiner* — Kiho Kim
(74) *Attorney, Agent, or Firm* — Oblon, McClelland, Maier & Neustadt, L.L.P.

(57) ABSTRACT

According to one embodiment, an X-ray diagnostic apparatus includes a couch, an imaging unit, and processing circuitry. The couch includes a couch top on which a subject lies. The imaging unit includes an X-ray generator, an X-ray detector, and a holding device. The holding device movably holds the X-ray generator and the X-ray detector. The processing circuitry generates an X-ray image of the subject, based on an output of the X-ray detector, sets a first interference determination area including a device projecting from the subject, based on an image of the device included in the X-ray image, and controls the holding device such that movement of the imaging unit is restricted in the first interference determination area.

20 Claims, 14 Drawing Sheets

(52) U.S. Cl.
CPC ............ *A61B 6/4447* (2013.01); *A61B 6/504* (2013.01); *A61B 6/5205* (2013.01)

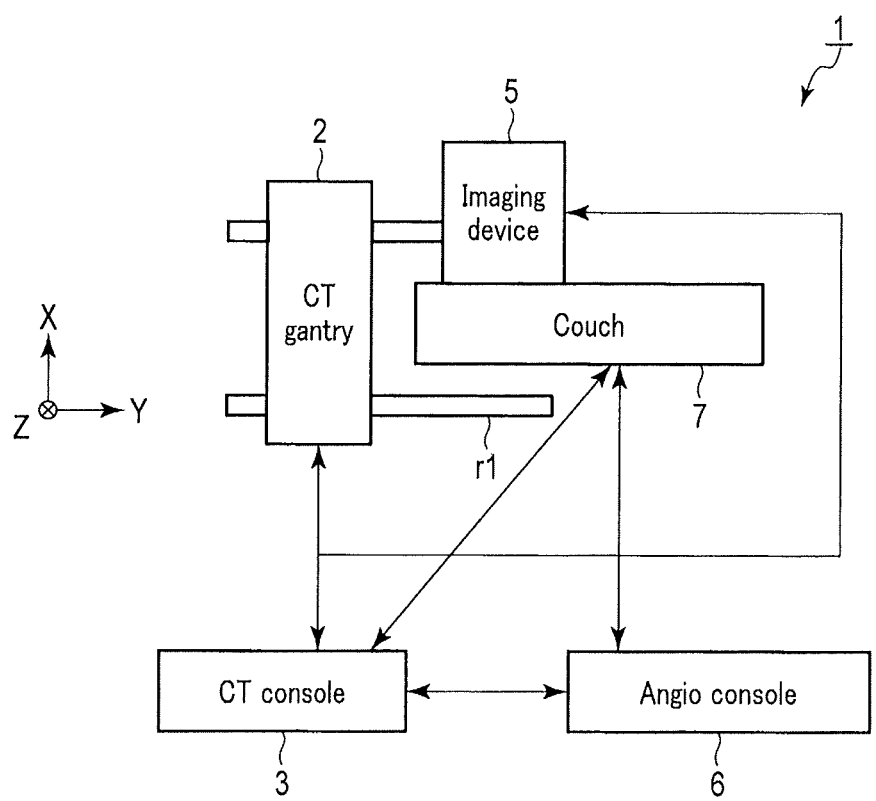
F I G. 2

| Identification information of needle | Overall length of needle [mm] |
|---|---|
| needle1 | 25 |
| needle2 | 100 |
| needle3 | 200 |
| ⋮ | ⋮ |

65a

F I G. 3B

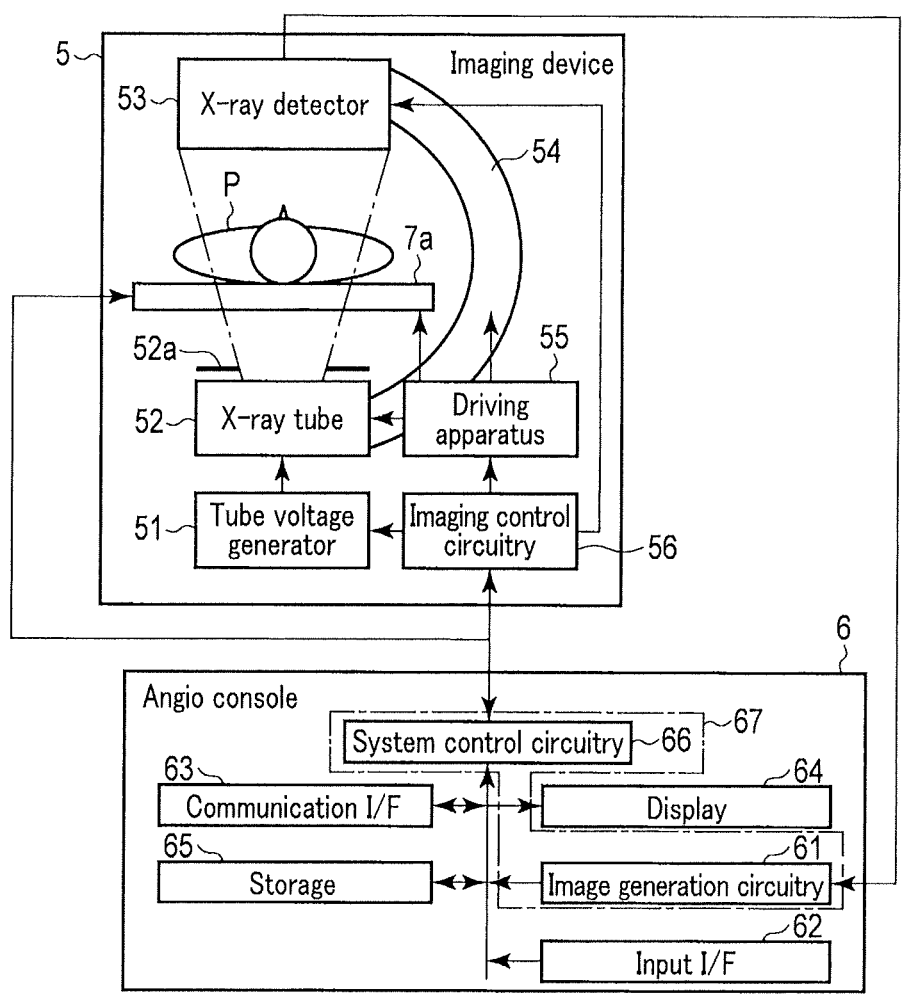
F I G. 10

X-RAY DIAGNOSTIC APPARATUS, MEDICAL IMAGE DIAGNOSTIC SYSTEM AND CONTROL METHOD

CROSS-REFERENCE TO RELATED APPLICATIONS

This application is based upon and claims the benefit of priority from prior Japanese Patent Applications No. 2016-245565, filed on Dec. 19, 2016, and No. 2017-219221, filed on Nov. 14, 2017, the entire contents of all of which are incorporated herein by reference.

FIELD

Embodiments described herein relate generally to an X-ray diagnostic apparatus, a medical image diagnostic system, and a control method.

BACKGROUND

An X-ray diagnostic apparatus for interventional radiology includes an interference preventing function of preventing a movable body, such as a C arm, from coming into contact with a subject and a couch. A medical image diagnostic system is known which alternately uses this type of X-ray diagnostic apparatus and another modality (medical diagnostic apparatus). As the second modality, a computed tomography (CT) apparatus or a magnetic resonance imaging (MRI) apparatus can be used. Where the second modality is a CT apparatus, the medical image diagnostic system is referred to as an "angio-CT apparatus" or an "angio-CT system" as well. There may be a case where this type of X-ray diagnostic apparatus and the medical image diagnostic system are used for inserting a paracentesis needle into the subject in order to take a tissue piece of a tumor and to perform an ablation treatment.

In this case, the medical image diagnostic system advances the inserted paracentesis needle to a target portion under the fluoroscopic guidance by the X-ray diagnostic apparatus, and then performs auto-positioning. By this operation, the units of the X-ray diagnostic apparatus, including the holding device and the couch, are retracted to their respective target positions, and the CT gantry of the CT apparatus is positioned. The auto-positioning is a function of automatically moving the units of the X-ray diagnostic apparatus to the target positions in response to the input of unit identification information (e.g., a number) and the operation of a trigger switch, with the target positions of the units of the X-ray diagnostic apparatus and the unit identification information being associated and registered beforehand. In the case of the angio-CT system, the CT gantry can be positioned simultaneously with the movement of the units of the X-ray diagnostic apparatus. After the CT gantry is positioned, the CT apparatus performs imaging for confirmation.

Although the medical image diagnostic system mentioned above normally causes no problem, the inventor took into consideration that the X-ray diagnostic apparatus or the CT gantry might collide with the paracentesis needle if the auto-positioning is performed without reference to the paracentesis needle projecting from the body surface of the subject. To avoid this collision, the auto-positioning is not performed, and positioning based on a manual operation is performed paying attention to the position of the paracentesis needle. Such positioning is troublesome and takes time. This problem is not limited to the case of the paracentesis needle but holds true for some kind of device projecting from the subject. In addition, the problem is not limited to the case of the medical image diagnostic system but holds true for the case of an X-ray diagnostic apparatus used alone, which temporarily retracts the holding device to its target position and then performs auto-positioning to return the holding device to the imaging position.

Accordingly, an object is to prevent collision with a device projecting from the subject and to alleviate the labor and time in positioning.

BRIEF DESCRIPTION OF THE DRAWINGS

FIG. 1 is a perspective view showing how a medical image diagnostic system according to a first embodiment looks like.

FIG. 2 is a block diagram illustrating a schematic configuration of the medical image diagnostic system of the embodiment.

FIG. 3B is a schematic diagram illustrating a table used in the embodiment.

FIG. 10 is a block diagram illustrating a configuration of an X-ray diagnostic system according to a second embodiment.

DETAILED DESCRIPTION

In general, according to one embodiment, an X-ray diagnostic apparatus includes a couch, an imaging unit, and processing circuitry.

The couch includes a couch top on which a subject lies.

The imaging unit includes an X-ray generator, an X-ray detector, and a holding device.

The X-ray generator is configured to radiate X-rays to the subject.

The X-ray detector is configured to detect X-rays transmitted through the subject.

The holding device movably holds the X-ray generator and the X-ray detector.

The processing circuitry is configured to: generate an X-ray image of the subject, based on an output of the X-ray detector; set a first interference determination area including a device projecting from the subject, based on an image of the device included in the X-ray image; and control the holding device such that movement of the imaging unit is restricted in the first interference determination area.

A description will now be given of embodiments with reference to the accompanying drawings.

First Embodiment

Figure 1:
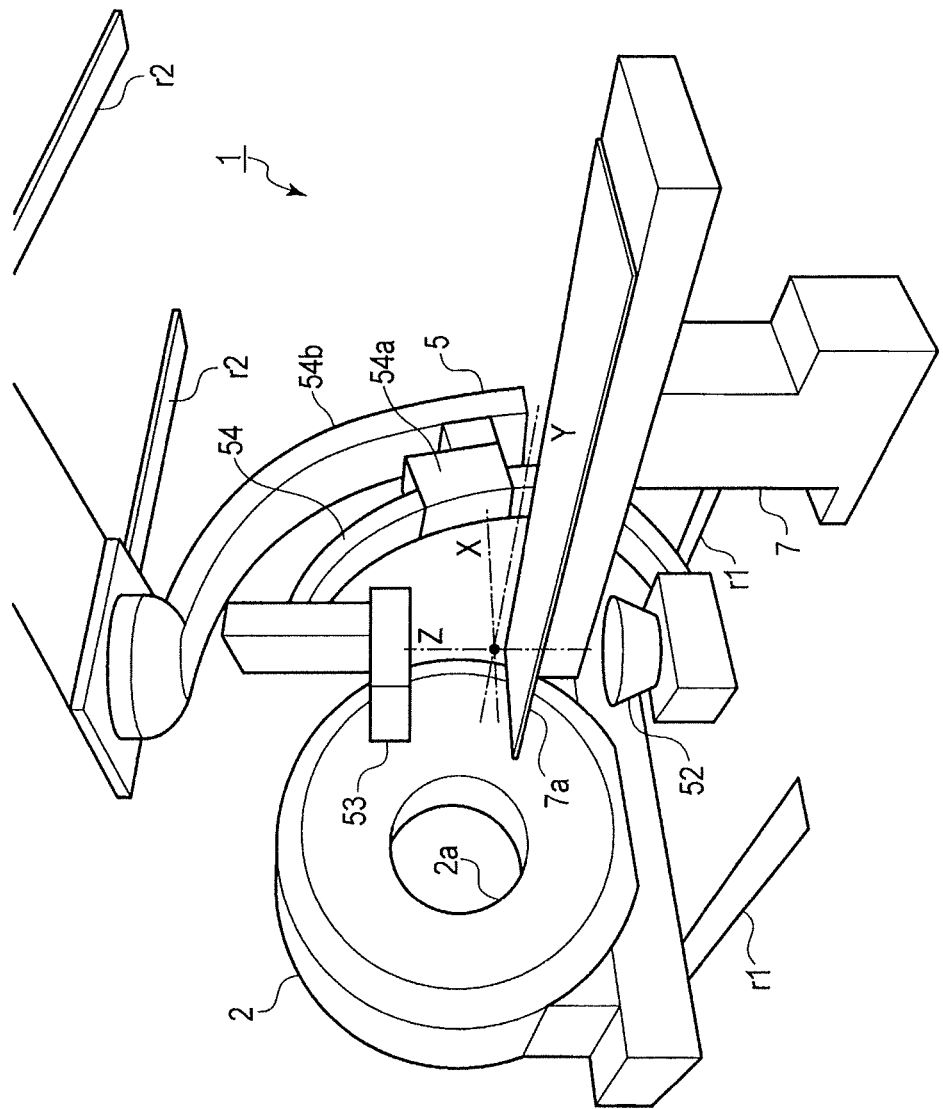

FIG. 1 is a perspective view showing how a medical image diagnostic system according to a first embodiment looks like, and FIG. 2 is a block diagram illustrating a schematic configuration of the medical image diagnostic system. The medical image diagnostic system 1 is an angio-CT system including a CT gantry 2, a CT console 3, an imaging device 5, an angio console 6 and a couch 7. The CT console 3 and the angio console 6 may be integrated as a single console. The angio-CT system is an example of a medical image diagnostic system. The medical image diagnostic system may replace the CT apparatus with another modality. Such an alternative modality is, for example, an MRI apparatus. The alternative modality is not limited to this, and any modality may be used as long as it is used alternately with the imaging device 5 and can be moved closer to or away from a subject P. The "imaging device 5" may be referred to as an "angio device 5."

The CT gantry 2 includes an opening 2a through which the couch top 7a of the couch 7 is inserted, and the CT gantry 2 is movable on a plurality of rails r1 provided on the floor and extending in the long-axis direction of the couch top 7a.

The imaging device 5 is movable in the long-axis direction or short-axis direction of the couch top 7a under a plurality of rails r2 provided on the ceiling. In addition, the imaging device 5 can be moved between the rails r2 in the long-axis direction and short-axis direction of the couch top 7a by a movement mechanism (not shown).

The imaging device 5 includes: a C arm 54 which has an X-ray tube 52 at one end and an X-ray detector 53 at the other end; a holding unit 54a which holds the C arm 54; and a support arm 54b which supports the holding unit 54a at the distal end. The support arm 54b has a substantially arc shape, and the proximal end of the support arm 54b is attached to a movement mechanism facing the rails r2. The C arm 54 is held by the holding unit 54a such that it is rotatable around an X-direction axis, which is perpendicular to both a Z direction perpendicular to the couch top 7a and a Y direction along the long-axis direction of the couch top 7a. The C arm 54 has a substantially arc shape having a Y-direction axis as a center, and is held by the holding unit 54a such that the C arm 54 is slidable along the substantially arc shape. Alternatively, the C arm 54 can be rotated around an X-direction axis, with the holding unit 54a as a center, and thus enables an X-ray image to be observed in various angular directions determined by the sliding movement and the rotating movement.

The couch 7 includes a couch top 7a which is used in common to both the CT gantry 2 and the imaging device 5 and on which a subject lies. The couch 7 holds the couch top 7a such that the couch top 7a is movable in the vertical direction. The couch top 7a is held such that it is movable in the long-axis direction thereof or in the short-axis direction thereof and is rotatable around a Y-direction axis. The couch 7 used in common is controlled by system control circuitry 37 of the CT console 3 and system control circuitry 66 of the angio console 6.

Next, a specific description will be given of the configuration of the medical image diagnostic apparatus.

Figure 3A:
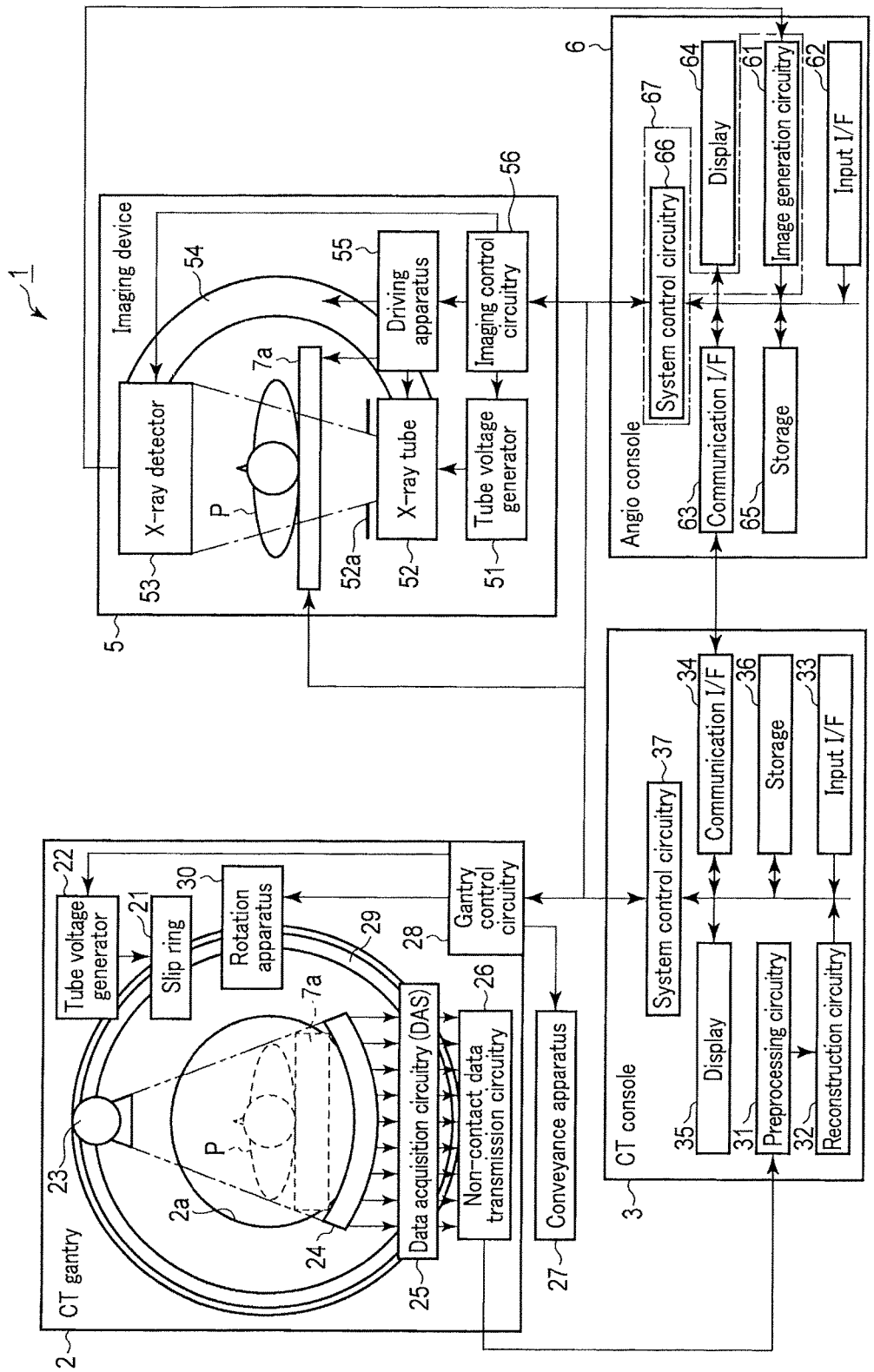
FIG. 3A is a block diagram illustrating a configuration of the medical image diagnostic system of the embodiment.

FIG. 3A is a block diagram showing the configuration of the medical image diagnostic system. The CT apparatus, constituting part of the medical image diagnostic system 1, comprises a CT gantry 2, a CT console 3 and a couch 7. The CT gantry 2 includes a slip ring 21, a tube voltage generator 22, an X-ray tube 23, an X-ray detector 24, data acquisition circuitry 25 (namely, a data acquisition system (DAS)), non-contact data transmission circuitry 26, a conveyance apparatus 27 and gantry control circuitry 28. The CT gantry 2 also includes a rotation ring 29, a ring support mechanism which supports the rotation ring 29 such that the rotation ring 29 is freely rotatable, with the body axis (Z axis) of the subject as the axis of rotation, and a rotating apparatus (electric motor) which rotates the rotation ring 29. The rotation ring 29 is received in the CT gantry 2 and holds the X-ray tube 23 and the X-ray detector 24, which are arranged opposite to each other with the opening 2a therebetween. The couch top 7a, on which the subject P can lie 31, is inserted through the opening of the rotation ring 29. The couch top 7a is supported by the couch 7 so as to be movable along the central axis of the rotation ring 29. The couch top 7a is positioned such that the body axis of the subject P lying on the couch top 7a coincides with the central axis of the rotation ring 29. The tube voltage generator 22, the X-ray tube 23, the X-ray detector 24, the DAS 25, the non-contact data transmission circuitry 26, a cooling apparatus (not shown), etc. are installed on the rotation ring 29. Under the control of the CT console 3 using the gantry control circuitry 28, the tube voltage generator 22 generates a tube voltage to be applied to the X-ray tube 23 and a filament current to be supplied to the X-ray tube 23.

The X-ray tube 23 is applied with the tube voltage and supplied with the filament current by the tube voltage generator 22 through the slip ring 21. The X-ray tube 23 radiates X-rays from the X-ray focus toward the subject P lying on the couch top 7a. The X-ray tube 23 generates X-rays having an energy spectrum corresponding to the tube voltage applied by the tube voltage generator 22. The irradiation range of the X-rays is indicated by the long dashed double-short dashed line in FIG. 3A.

The X-ray detector 24 is attached to the rotation ring 29 at such a position and angle as permit the X-ray detector 24 to be opposed to the X-ray tube 23, with the axis of rotation in between. The X-ray detector 24 includes a plurality of light-receiving bands for detecting X-rays radiating from the X-ray tube 23. In the description below, it is assumed that one light-receiving band constitutes one channel. The channels are perpendicular to the axis of rotation and are arranged in two dimensions in the arc direction (channel direction) and the Z direction (slice direction). The radius of the arc is defined as the distance between the focus of the radiating X-rays and the center of a one-channel receiving band. The DAS 25 is connected to an output side of the X-ray detector 24. The X-ray detector 24 arranges the light-receiving bands in one row. At this time, the light-receiving bands are arranged in one dimension and extend in a substantially arc direction which is along the channel direction. The light-receiving bands may be arranged in two dimensions with respect to the channel direction and the slice direction. That is, the two-dimensional arrangement is formed by a plurality of arrays each of which includes channels arranged in one dimension in the channel direction and which are arranged in the slice direction.

The DAS 25 comprises an IV converter which converts a current signal of each channel of the X-ray detector 24 to a voltage signal, an integrator which periodically integrates the voltage signal in synchronism with radiation periods of X-rays, an amplifier which amplifies an output signal of the integrator, and an analog-to-digital converter which converts an output signal of the amplifier to a digital signal. These elements of the DAS 25 are provided for each of the channels. The DAS 25 transmits output data (pure raw data) to the CT console 3 through the non-contact data transmission circuitry 26 using magnetic transmission/reception or optical transmission/reception.

The conveyance apparatus 27 conveys the CT gantry 2 to and from the couch 7. The conveyance apparatus 27 uses, for example, a rail L1 installed on the floor of an inspection room, to convey the CT gantry 2.

The gantry control circuitry 28 has the function of controlling the tube voltage generator 22, conveyance apparatus 27, rotation apparatus 30, etc. of the CT gantry 2, in accordance with control signals supplied from the CT console 3. The gantry control circuitry 28 includes, as hardware resources, a processor such as a CPU or an MPU and a memory such as a ROM or a RAM. The gantry control circuitry 28 may be realized by an ASIC, an FPGA, a CPLD, an SPLD, or the like. The processor reads the programs stored in the memory and executes them to realize the functions mentioned above. The programs may be incorporated in the circuitry of the processor, instead of storing them in the memory. In this case, the processor reads the programs incorporated in its circuitry and executes them to realize the functions.

The CT console 3 comprises preprocessing circuitry 31, reconstruction circuitry 32, an input interface (I/F) 33, a communication interface (I/F) 34, a display 35, a storage 36 and system control circuitry 37.

The preprocessing circuitry 31 performs preprocessing for the pure raw data output from the non-contact data transmission circuitry 26. The preprocessing includes, for example, processing for logarithmic conversion of the pure raw data, processing for correcting non-uniformity in sensitivity of channels, and processing for correcting an extreme decrease in signal intensity due to a strong absorber of X-rays, in particular, a metal part, or processing for correcting signal omission. The preprocessing circuitry 31 associates data which is subjected to the preprocessing and is to be subjected to reconstruction processing (such data is referred to as raw data or projection data, and will be referred to as projection data herein) with data representing the view angle at which the data is collected, and transmits the resultant data to the reconstruction circuitry 32 and the storage 36.

The projection data is a set of data values corresponding to the intensities of the X-rays transmitted through the subject P. For convenience of explanation, the projection data which is collected substantially simultaneously by one shot and obtained from all channels at the same view angle will be referred to as a projection data set. The view angle indicates where the X-ray tube 23 rotating around the axis of rotation is located on the circular track, and with the top position of the circular track (which is vertically upward from the axis of rotation) being regarded as 0°, the view angle is expressed in the angular range of 0° to 360°. The projection data included in the projection data set and corresponding to each channel is identified by a view angle, a cone angle and a channel number.

Based on the projection data sets transmitted from the preprocessing circuitry 31 and collected, for example, in the angular range of 360° or 180°+(fan angle), the reconstruction circuitry 32 reconstructs volume data on a substantially cylindrical region, using the Feldkamp method, the iterative approximation reconstruction method, or the like. The reconstruction circuitry 32 is realized, for example, by a memory and a predetermined processor. The reconstruction circuitry 32 reconstructs a three-dimensional image (volume data, which will be hereinafter referred to simply as a 3D image) from the projection data sets mentioned above. The Feldkamp method is used where projection rays intersect the reconstruction plane, just like cone beams. Assuming that the cone angle is small, the projection can be regarded as fan beam projection, and the reconstruction processing can be performed at high speed. The reconstruction circuitry 32 transmits the reconstructed 3D image to the storage 36.

The input interface 33 is realized by a trackball, a switch button, a foot switch, a mouse, a keyboard, a touch pad through which an input operation can be carried out by a touch of an operation surface, a touch panel display which is an integrated combination of a display screen and a touch pad, etc. The input interface 33 is connected to the system control circuitry 37. The input interface 33 converts an input operation received from the operator into an electric signal, and outputs the electric signal to the system control circuitry 37. In the present embodiment, the input interface 33 is not limited to circuitry provided with a physical operation component, such as a trackball, a switch button, a foot switch, a mouse, or a keyboard. For example, the input interface 33 may include electric signal processing circuitry which receives an electric signal corresponding to an input operation through an external input device separate from the apparatus, and supplies that electric signal to the system control circuitry 37.

The communication interface 34 is circuitry which communicates with an external apparatus by wire and/or wireless. The external apparatus is, for example, a modality, a server included in a radiological information system (RIS), a hospital information system (HIS), a picture archiving and communication system (PACS) or the like, or a work station.

The display 35 includes a main display device which displays medical images, etc. under the control of the system control circuitry 37, internal circuitry which supplies display signals to the main display device, and peripheral circuitry including connectors, cables, etc. to connect the main display device and the internal circuitry.

The storage 36 includes a memory for storing electric information, such as a read-only memory (ROM), a random access memory (RAM), a hard disk drive (HDD), or an image memory, and peripheral circuitry associated with the memory, such as a memory controller and a memory interface. The storage 36 stores projection data transmitted from the preprocessing circuitry 31 and 3D images reconstructed by the reconstruction circuitry 32. The storage 36 also stores a control program for controlling the timing at which a tube voltage is applied to the X-ray tube 23.

A storage area of the storage 36 may be within the medical image diagnostic system 1 or within an external storage device connected via the network.

The system control circuitry 37 comprises a processor and a memory (neither shown in the drawings). The system control circuitry 37 functions as a center of the CT apparatus. To be specific, the system control circuitry 37 reads the control program stored in the storage 36 and loads it in the memory, and controls the portions of the CT apparatus in accordance with the loaded control program. The system control circuitry 37 also controls the couch 7, based on operator's instructions supplied from the input interface 33.

Next, a description will be given of the angio system of the medical image diagnostic system 1. The angio system comprises an imaging device 5, an angio console 6 and a couch 7 used by the CT apparatus as well.

The imaging device 5 includes a tube voltage generator 51, an X-ray tube 52, an X-ray detector 53, a C arm 54, a holding unit 54a, a support arm 54b, a driving apparatus 55, and imaging control circuitry 56.

The tube voltage generator 51 generates a tube current to be supplied to the X-ray tube 52 and a tube voltage to be applied to the X-ray tube 52. Under the control of the angio console 6 using the imaging control circuitry 56, the tube voltage generator 51 supplies the tube current to the X-ray tube 52 and applies the tube voltage to the X-ray tube 52 in accordance with the X-ray imaging conditions.

The X-ray tube 52 generates X-rays at the X-ray focus, based on the tube current supplied from the tube voltage generator 51 and the tube voltage applied by the tube voltage generator 51. The X-rays generated at the X-ray focus is radiated to the subject P by way of an X-ray radiation window provided in front of the X-ray tube 52. Part of the X-rays generated at the X-ray focus are shielded by a collimator 52a, provided between the X-ray tube 52 and the X-ray radiation window.

The X-ray detector 53 detects the X-rays generated by the X-ray tube 52 and transmitted through the subject P. Electric signals which a plurality of semiconductor detection elements generate in response to the incidence of X-rays are output to an analog-to-digital converter (ADC), not shown. The ADC converts the electric signals into digital data. The ADC supplies the digital data to image generation circuitry 61. An image intensifier may be used as the X-ray detector 53.

A support mechanism (holding device), including the C arm 54, the holding unit 54a and the support arm 54b, movably supports the X-ray tube 52 and the X-ray detector 53. To be specific, the C arm 54 permits the X-ray tube 52 and the X-ray detector 53 to face each other. The holding unit 54a supports the C arm 54 such that the C arm 54 is slidable in the direction along the C shape of the C arm 54 (the direction will be referred to as the C direction). The support arm 54b for holding the holding unit 54a is movable along a rail L2 provided on the ceiling. The rail L2 provided on the ceiling extends, for example, in the long-axis direction of the couch top 7a or in the short-axis direction thereof. The holding unit 54a holds the C arm 54 such that the C arm 54 is rotatable in a direction perpendicular to the C direction (hereinafter referred to as a C perpendicular direction), with the connection portion between the C arm 54 and the support arm 54b being a substantial center. The C arm 54 supports the X-ray tube 52 and the X-ray detector 53 such that the distance between the X-ray focus and the X-ray detector 53 (a source image distance (SID)) can be varied.

The C arm 54 is not limited to the support mechanism constituted by both the holding unit 54a and the support arm 54b. The C arm 54 may be supported by a support column that is movable on the floor surface. Alternatively, the C arm 54 may be supported, for example, by a multi-joint arm of an industrial robot such that the C arm 54 can be moved in any direction desired. Alternatively, the C arm 54 may be movably provided on the floor, in place of the structure hanging from the ceiling. In addition, the C arm 54 may have a biplane structure.

The driving apparatus 55 drives the couch 7, the C arm 54, the holding unit 54a and the support arm 54b under the control of the angio console 6. To be specific, the driving apparatus 55 supplies the holding unit 54a with a driving signal corresponding to a control signal supplied from the system control circuitry 66, so as to slide the C arm in the C direction and rotate it in the C perpendicular direction. During the X-ray imaging, the subject P lying on the couch top 7a is located between the X-ray tube 52 and the X-ray detector 53.

The driving apparatus 55 drives the couch 7 to move the couch top 7a, under the control of the system control circuitry 66. To be specific, the driving apparatus 55 slides the couch top 7a in the short-axis direction of the couch top 7a or in the long-axis direction thereof, based on control signals supplied from the system control circuitry 66. The driving apparatus 55 moves the couch top 7a in the vertical direction. In addition, the driving apparatus 55 may incline the couch top 7a by rotating it, with at least one of the long-axis direction and the short-axis direction being the axis of rotation.

The imaging control circuitry 56 controls the tube voltage generator 51, the X-ray detector 53, the driving apparatus 55, etc., in accordance with control signals which the system control circuitry 66 supplies based on the operator's instructions, the X-ray imaging direction, the X-ray irradiation range, the X-ray irradiation conditions, etc.

The angio console 6 comprises image generation circuitry 61, an input interface 62, a communication interface 63, a display 64, a storage 65 and system control circuitry 66. The image generation circuitry 61 and the system control circuitry 66 may be integrated as processing circuitry 67 that is a hardware element. In other words, the image generation circuitry 61 and the system control circuitry 66 may be realized by the processing circuitry 67. The processing circuitry 67 may be a processor which reads processing programs stored in the storage 65 and executes them so as to realize the image generation circuitry 61 and system control circuitry 66 corresponding to the programs. This holds true for each of the embodiments and modifications described below.

The image generation circuitry 61 performs preprocessing for digital data output from the X-ray detector 53. The preprocessing includes, for example, processing for correcting non-uniformity in sensitivity of the channels of the X-ray detector 53 and processing for correcting an extreme decrease in signal intensity due to a strong absorber of X-rays, in particular, a metal part, or processing for correcting signal omission. The image generation circuitry 61 has the function of generating an X-ray image based on the digital data subjected to the preprocessing. The image generation circuitry 61 supplies the generated X-ray image to the display 64 and the storage 65.

The input interface 62 is realized by a trackball, a switch button, a foot switch, a mouse, a keyboard, a touch pad through which an input operation can be carried out by a touch of an operation surface, a touch panel display, which is an integrated combination of a display screen and a touch pad, etc. The input interface 62 is connected to the system control circuitry 66. The input interface 62 converts an input operation received from the operator into an electric signal, and outputs the electric signal to the system control circuitry 66. In the present embodiment, the input interface 62 is not limited to circuitry provided with a physical operation component, such as a trackball, a switch button, a foot switch, a mouse, or a keyboard. For example, the input interface 62 also includes electric signal processing circuitry which receives an electric signal corresponding to an input operation through an external input device separate from the apparatus, and supplies the electric signal to the system control circuitry 66.

The communication interface 63 is circuitry which communicates with an external apparatus by wire and/or wireless. The external apparatus is, for example, a modality, a server included in a radiological information system (RIS), a hospital information system (HIS), a PACS or the like, or a work station.

The display 64 includes a main display device which displays medical images, etc. under the control of the system control circuitry 66, internal circuitry which supplies display signals to the main display device, and peripheral circuitry including connectors and cables to connect the main display device and the internal circuitry to each other.

The storage 65 includes a memory which stores electric information, such as a ROM, a RAM, an HDD or an image memory, and peripheral circuitry associated with the memory, such as a memory controller and a memory interface. The storage 65 stores X-ray images generated by the image generation circuitry 61, control programs of the imaging device 5, a paracentesis assistance program, an imaging protocol, operator's instructions entered from the input interface 62, various data on the imaging conditions and fluoroscopy conditions regarding the X-ray imaging, X-ray doses, etc. The storage 65 also stores size information (a semi-cylindrical shape model) regarding the subject P and used for the interference prevention function, size information on the imaging system and the C arm 54, and size information on the couch top 7a. The size information is used for specifying the position and size of an interfering object, together with the position information on the imaging system and the C arm 54 and the position information on the couch top 7a. The storage 65 may hold information on the overall length of a needle preset beforehand. The overall length of the needle may be set at any value, for example, 25 mm, 100 mm, or 200 mm. The overall length of the needle may be associated, for example, with needle identification information (e.g., a name, a product number, a product code or a model number). This setting is applicable not only to the case where a single needle is used but also to the case where a plurality of needles are used. As shown in FIG. 3B, the storage 65 may store a table 65a in which the overall length of a needle and a setting flag are associated for each needle identification information beforehand. The setting flag may be determined such that value "1" represents being valid and value "0" represents being invalid. In this case, one of the values of the overall length of the needle may be set as a default value, or the overall length corresponding to the needle identification information designated from the input interface 62 may be set. Alternatively, one of the values of the overall length of the needle may be set as a default value, and when the needle identification information is designated, the overall length corresponding to the designated needle identification information may be set (updated), instead of the default value. Where the storage 65 stores a plurality of values of the overall length, setting the overall length is determining setting flags related to the overall length. Where the storage 65 stores one value of the overall length, setting the overall length is equivalent to storing the overall length. The table 65a may be updated on a regular or irregular basis in accordance with the database (not shown) of the approval information on the medical devices based on law or the like. The table 65a may be updated by the user's operation of the input interface 62 or by the execution of an updating program. The type of needle is selected in accordance with the purpose, and the needle may be a "paracentesis needle", a "biopsy needle", a "transplantation needle", an "ablation needle", an "electrode needle", or the like. In each of the embodiments described below, a paracentesis needle will be mentioned as an example of the needle.

Figure 4:
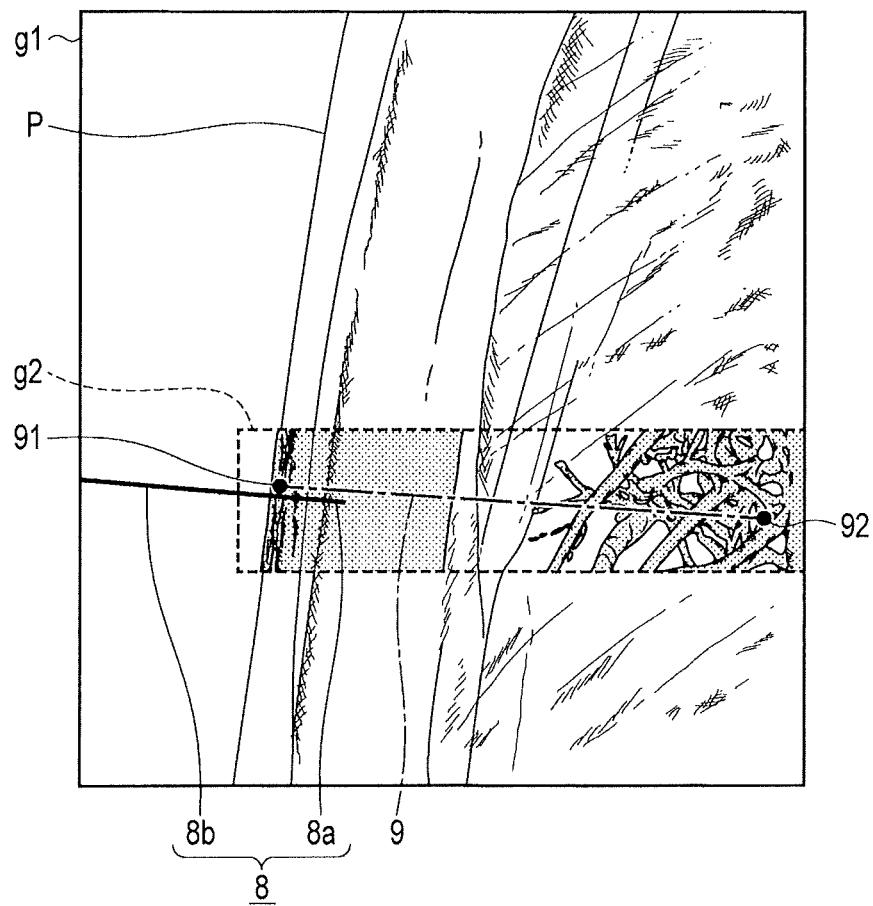
FIG. 4 is a schematic diagram illustrating the paracentesis assistance function used in the embodiment.

The system control circuitry 66 comprises a processor and a memory (neither shown in the drawings). The system control circuitry 66 temporarily stores information on operator's instructions supplied from the input interface 62, an X-ray imaging position, an X-ray imaging direction of the X-ray tube 52, an X-ray irradiation range, X-ray irradiation conditions, etc. in the memory not shown in the drawings. In order to execute X-ray imaging in accordance with the operator's instructions, X-ray imaging direction, X-ray irradiation range, X-ray irradiation conditions, etc., the system control circuitry 66 causes the imaging control circuitry 56 to control the tube voltage generator 51, the X-ray detector 53, the driving apparatus 55, the couch 7, etc. In addition, the system control circuitry 66 can realize the paracentesis assistance function by executing the paracentesis assistance program. In the surgical procedure of inserting a paracentesis needle from the body surface of the subject P for the purpose of taking a tissue piece of a tumor or performing an ablation treatment, the paracentesis needle 8 has to be advanced accurately, as shown in FIG. 4. The paracentesis assistance function is a function of executing a paracentesis plan and performing navigation of the paracentesis procedure under the X-ray fluoroscopy so as to perform the surgical procedure accurately. The paracentesis plan includes designating a path 9 connecting a paracentesis portion 91 and a target portion 92 and determining two working angles. The paracentesis portion 91 and the target portion 92 may be interpreted as a paracentesis position and a target position, respectively. The distance between the paracentesis portion 91 and the target portion 92 may be displayed in the neighborhood of the path 9. In the path 9 shown in FIG. 4, the distance such as "80.00 mm" may be displayed above the path 9. The distance can be displayed in the neighborhood of the path 9 in this manner, and this feature holds true for FIGS. 5 and 6 as well. The navigation includes processing of superimposing part of a 3D image g2 on an X-ray image g1 (which is an X-ray fluoroscopic image), and processing of displaying the path 9 on the superimposed 3D image g2. In FIG. 4, the linear line on the right side of the paracentesis portion 91 indicates that portion 8a of the paracentesis needle 8 which is located inside the subject P. The linear line on the left side of the paracentesis portion 91 indicates that portion 8b of the paracentesis needle 8 which projects from the body surface of the subject P.

The two working angles correspond to the angles by which the C arm 54 is inclined relative to the vertical axis. The working angles are a parallel viewing angle and a vertical viewing angle, and are alternately switched during the paracentesis so that the state of the paracentesis needle 8 can be confirmed.

Figure 5:
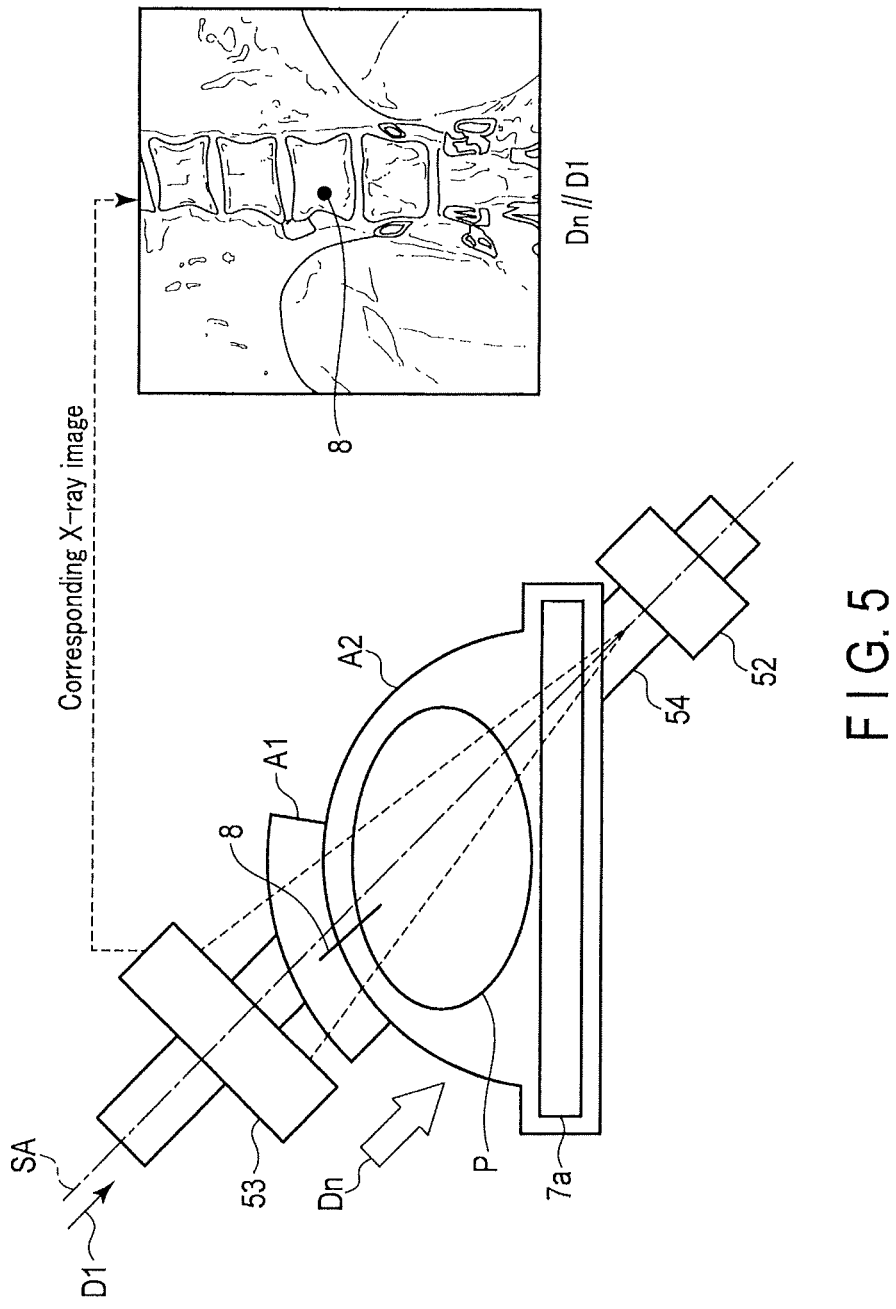
FIG. 5 is a schematic diagram illustrating how a direction parallel to a path is in the embodiment.

The parallel viewing angle is a viewing angle corresponding to direction D1 which is parallel to direction Dn of the path, as shown in the left portion of FIG. 5. When the C arm 54 is set at the parallel viewing angle, the axis direction of the imaging axis SA is substantially parallel to direction Dn of the path. The imaging axis SA is an axis passing through the X-ray focus of the x-ray tube 52 and the center of the detection surface of the X-ray detector 53. In an X-ray image taken at the parallel viewing angle, the paracentesis needle 8 is displayed as a dot or a short linear line, as shown in the right portion of FIG. 5. Where the paracentesis needle 8 is displayed as a dot, the paracentesis needle 8 is inserted along the path 9 (not shown in FIG. 5). On the other hand, where the paracentesis needle 8 is displayed as a short linear line, it can be seen that the paracentesis needle 8 is inserted in a direction shifted from the path 9.

Figure 6:
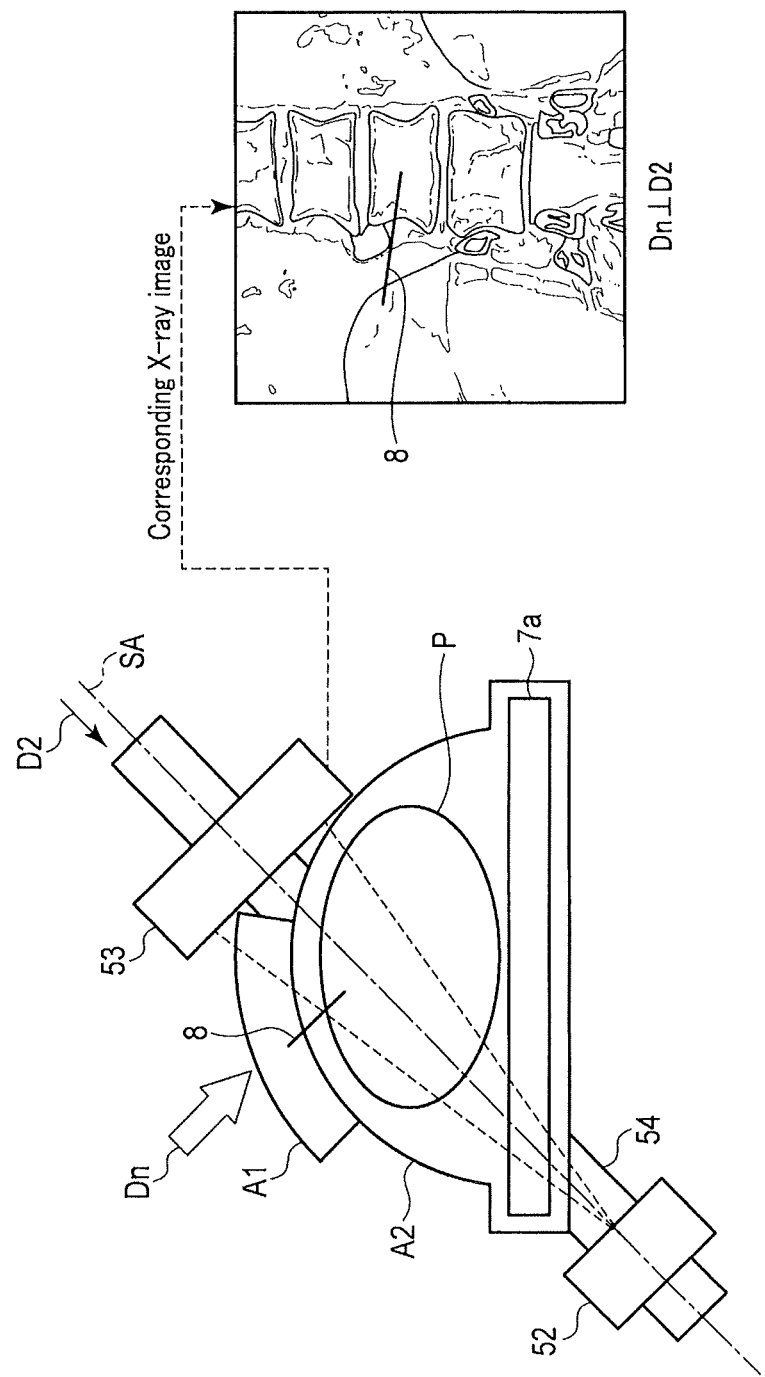
FIG. 6 is a schematic diagram illustrating how a direction perpendicular to a path is in the embodiment.

The vertical viewing angle is a viewing angle corresponding to direction D2 which is perpendicular to direction Dn of the path, as shown in the left portion of FIG. 6. When the C arm 54 is set at the vertical viewing angle, the axis direction of the imaging axis SA is substantially perpendicular to direction Dn of the path. In an X-ray image taken at the vertical viewing angle, the paracentesis needle 8 is displayed as a long linear line, as shown in the right portion of FIG. 6. In the X-ray image shown in FIG. 6, the paracentesis needle 8 overlaps the path 9 (not shown in FIG. 6).

The system control circuitry 66 has an interference preventing function including an updating function. The updating function is a function of updating a second interference determination area A2 including both the couch top 7a and the subject P as shown in FIGS. 5 and 6, based on the geometric imaging conditions of an X-ray image. To be specific, the updating function derives the position and size of the couch top 7a and those of the subject P, based on the geometric imaging conditions of the X-ray image, and updates the second interference determination area A2 based on the derived results. It should be noted that the updating function is a function that can be added as an option; the updating function may be omitted, if so desired. The interference preventing function updates the second interference determination area A2 by use of the updating function and controls at least the movement of the imaging device 5, based on the updated second interference determination area A2. For example, if the clearance between a moving object and an interfering object becomes a threshold value or less, the interference preventing function generates warning sound or decelerates or stops the movements of the CT gantry 2 and the imaging device 5. Even if the updating function is omitted, the interference preventing function can control at least the movement of the imaging device 5, based on the second interference determination area A2 that is not updated. The system control circuitry 66 controls the display 64, etc.

In addition to the control described above, the system control circuitry 66 sets a first interference determination area including a device projecting from the subject P, based on the image of the device included in the X-ray image, and controls the holding device such that the movement of the imaging device 5 is restricted in that first interference determination area. The holding device is a support mechanism including the C arm 54, the holding unit 54a and the support arm 54b. Where the movement of the imaging device 5 is restricted in the first interference determination area, the movement of the imaging device 5 may be restricted such that the imaging device 5 does not enter the first interference determination area. Alternatively, the movement of the imaging device 5 may be restricted such that the moving speed of the imaging device is lower in the first interference determination area than in the areas other than the first interference determination area. In other words, the system control circuitry 66 may control the holding device such that the movement of the imaging device 5 is stopped or decelerated in the first interference determination area. When the movement of the imaging device 5 is restricted, notification may be issued if the imaging device 5 enters the first interference determination area. In this case, the system control circuitry 66 may supplies a notification signal to a warning sound generator (not shown). The system control circuitry 66 may have functions (f66-1) to (f66-3) described below. The system control circuitry 66 may have a function in which function (f66-1) and function (f66-2) are combined. That is, the system control circuitry 66 may have a function of deriving how a device projects from the subject P and setting a first interference determination area based on the derived projection amount.

(f66-1): a deriving function of deriving a projection amount of a device from a subject P, based on the image of the device included in an X-ray image. In this example, the image of the device included in the X-ray image is an image of a paracentesis needle 8, and the device projecting from the subject is the paracentesis needle 8. The device is not limited to this type of needle, and may be any other type of needle which is inserted into the subject and part of which projects from the subject, such as a medical device needle used for taking a tissue piece or for performing an ablation treatment. To supplement the description, any type of medical device that is inserted into a subject can be used as the needle. This type of needle is, for example, a needle used for paracentesis, a needle used for ablation, a needle used for drainage, or a needle used for bone cement injection. This holds true for an image of a device (an image of a needle). The deriving function may be, for example, a function of deriving the length of a device inserted into a subject P from an image of the device, and subtracting the derived length from the overall length of the device set beforehand, thereby deriving a projection amount of the device from the subject P. In this case, the overall length of the device is stored in the storage 65 beforehand. That is, the system control circuitry 66 reads the overall length of the device which is set beforehand, and use the read overall length in the subtraction. The deriving function may derive the length of the device that is inserted into the subject P, based on the image of the device and the paracentesis plan. For example, the length of the image of the device inserted into the subject P and the length of the path 9 determined in the paracentesis plan are compared, and the length of the device advanced into the subject P can be derived from the result of comparison. The deriving function may start the derivation of a projection amount, with a predetermined operation by the operator as a trigger. The predetermined operation may be an operation of depressing a physical button or clicking an icon on a display. The deriving function may derive a projection amount in real time when the device is being advanced into the subject P. The state in which the device is advanced is, for example, a state in which the paracentesis needle 8 is inserted. The "real time" used here is intended to mean "at predetermined short intervals." That is, the "real time" can be called "virtually real time." When a projection amount is calculated in real time, all fluoroscopic images need not be used, and only part of sequentially generated fluoroscopic images may be used. For example, when fluoroscopic images are acquired at 30 fps, the processing for deriving a projection amount may be executed every 30 frames, and the setting of a first interference determination area may be repeatedly performed every second. In this case, the interval expressed by "at predetermined short intervals" is any interval from the updating interval of a fluoroscopic image (1/30 seconds) to the setting interval of a first interference determination area (1 second), namely, 0.033 to 1 second. For example, "at predetermined short intervals" means "at intervals of 0.5 seconds." If the projection amount of the device varies, the first interference determination area should be updated with no delay to a possible degree, but a short delay time is permissible. For example, a delay of 10 seconds or so is permissible. This is because 10 seconds or so are generally required after the end of the paracentesis based determined in a paracentesis plan and before the start of auto-positioning. In the meantime, the direction in which the paracentesis needle 8 is inserted and the depth to which the paracentesis needle 8 is inserted are confirmed. Where the setting of the first interference determination area is performed every 10 seconds or so, the latest first interference determination area is set and available at the start of the auto-positioning. The term "real time" means "at predetermined short intervals" and is not limited to any of the intervals of time (values of second) mentioned above.

(f66-2): a setting function of setting a first interference determination area A1 including a device (paracentesis needle 8) projecting from a subject P, as shown in FIG. 5 or FIG. 6, based on a derived projection amount. The setting function may set the first interference determination area A1 in real time provided that the projection amount is derived in real time. The "in real time" used here means "at predetermined short intervals", as mentioned above, but may indicate a longer interval than the "real time" mentioned in connection with the processing of deriving the projection amount. Where the first interference determination area A1 is set in real time, it does not have to be set for all projection amounts but may be set for only part of sequentially derived projection amounts. The first interference determination area A1 including the device and the second interference determination area A2 including both the couch top 7a and the subject P may be in contact with each other, with no overlap therebetween. Alternatively, the two areas A1 and A2 may overlap each other.

(f66-3): a control function of controlling the movement of the CT gantry 2, imaging device 5 and couch top 7a, while simultaneously preventing them from entering the set first interference determination area A1. For example, when the imaging device 5 is retracted from the imaging position, the control function moves the imaging device 5 such that the imaging device does not enter the first or second interference determination area A1 or A2. For example, when the CT gantry 2 is arranged at an imaging position, the control function controls the movement of the CT gantry 2 and the couch top 7a such that the CT gantry 2 and the couch top 7a do not enter the first or second interference determination area A1 or A2. For example, if the couch top 7a and the opening 2a are not at the same height, and the CT gantry 2 collides with the couch top 7a when it is moved toward the imaging position, the control function temporarily stops the CT gantry 2 and moves the couch top 7a in the vertical direction. By this operation, the control function moves the CT gantry 2 while simultaneously inserting the first and second interference determination areas A1 and A2 into the opening 2a of the CT gantry 2. For example, when the auto-positioning is being executed, the control function controls the movement of the CT gantry 2, imaging device 5 and couch top 7a such that these elements do not enter the first interference determination area A1 or the second interference determination area A2. The period in which the control function performs control is not limited to the period in which the auto-positioning is executed. In order to prevent the collision with a device projecting from a subject, the control function may perform control such that entry to at least the first interference determination area A1 is prevented, not entry to both the first and second interference determination areas A1 and A2.

The system control circuitry 66 may include an initialization function in addition to the functions mentioned above. The initialization function is a function of initializing the first interference determination area A1 (which becomes narrow as a result of repeated setting), with a predetermined condition as a trigger.

How the medical image diagnostic system having the above configurations operates will now be described with reference to the flowcharts shown in FIG. 7 and FIG. 8. In the description below, an image of a paracentesis needle will be mentioned as an example of an image of a device, and the paracentesis will be mentioned as an example of the device. This holds true for each of the embodiments and modifications described below.

In step ST1, the system control circuitry 37 of the CT console 3 sets the CT gantry 2 at an imaging position of a subject P lying on the couch top 7A. The imaging position is a position where a paracentesis portion 91 and a target portion 92 can be imaged.

In step ST2, the CT gantry 2 performs CT imaging, and a 3D image of the subject P is generated in the CT console 3 and displayed. If this 3D image has no problem, it is transferred from the CT console 3 to the angio console 6 and is stored in the storage 65 of the angio console 6. If the 3D image has a problem, step ST2 is executed once again.

In step ST3, the system control circuitry 66 of the angio console 6 executes a paracentesis assistance plan in response to an operation of the operator. In accordance with the paracentesis assistance plan, a 3D image in the storage 65 is displayed on the display 64, and a path 9 connecting the paracentesis position 91 and the target portion 92 is designated on the 3D image by an operation by the operator. Based on the designated path 9, a parallel viewing angle corresponding to direction D1 parallel to the direction Dn of the path 9 and a vertical viewing angle corresponding to direction D2 perpendicular to the direction Dn of the path 9 are determined.

In step ST4, the CT gantry 2 is retracted from the imaging position, and the imaging device 5 is set at a position close to the imaging position of the subject P.

When geometric imaging conditions of an X-ray image are entered by the operator, the system control circuitry 66 derives the positions and sizes of the couch top 7a and subject P from the imaging conditions in step ST5.

In step ST6, the system control circuitry 66 updates the second interference determination area A2 including both the couch top 7a and the subject P, based on the derived results.

In step ST7, the system control circuitry 66 controls the movement of the entire C arm 54 including both the X-ray tube 52 and the X-ray detector 53, based on the updated second interference determination area A2. For example, if the clearance between a moving object (the entire C arm 54) and an interfering object (the couch top 7a and the subject P) becomes a threshold value or less, the system control circuitry 66 causes the warning sound generator (not shown) to generate warning sound, or decelerates or stops the movement of the moving object. For example, a speaker or a buzzer may be used as the warning sound generator. In this manner, the X-ray tube 52 and the X-ray detector 53 are arranged in the neighborhood of the couch top 7a and the subject P, respectively, while simultaneously preventing the moving object from colliding with the interfering object. The closer the X-ray tube 52 and X-ray detector 53 are to the couch top 7a and subject P, the higher will be the quality of an X-ray image. It is therefore desired that X-ray imaging be performed with the X-ray tube 52 and the X-ray detector 53 being positioned as close as possible to the couch top 7a and the subject P. If the X-ray tube 52 and the X-ray detector 53 are too close, however, the risk of collision increases. As mentioned above, therefore, the movement of the moving object is controlled, with the warning sound being generated when necessary.

In step ST8, the imaging device 5 performs X-ray fluoroscopy and an X-ray image is generated. That is, the X-ray tube 52 generates X-rays to be radiated to the subject P, and the X-ray detector 53 detects X-rays transmitted through the subject P. The image generation circuitry 61 generates an X-ray image, based on outputs of the X-ray detector 53. The X-ray image is displayed on the display 64.

In step ST9, the system control circuitry 66 executes the paracentesis assistance program and activates the paracentesis assistance function, in response to an operation by the operator. The paracentesis assistance function controls the display 64 such that part of the 3D image including the path 9 designated in step ST3 is superimposed on the X-ray image displayed in step ST8. The system control circuitry 66 performs position adjustment between the X-ray image and the 3D image in accordance with an operation by the operator. After this position adjustment, the paracentesis is enabled.

In step ST10, the system control circuitry 66 sets the working angle at the parallel viewing angle, if necessary, and arranges the C arm 54 at an angle corresponding to the parallel viewing angle. If the C arm 54 is at the angle corresponding to the parallel viewing angle at the end of step ST9, step ST10 is omitted. At any rate, the paracentesis is started or continued under the X-ray fluoroscopy at the parallel viewing angle, at which the paracentesis portion 91 on the body surface of the subject P can be visually recognized with ease.

In step ST11, the angio console 6 generates an X-ray image of the paracentesis and displays it on the display 64. After the paracentesis, the control advances to step ST12.

In step ST12, the imaging device 5 is retracted from the imaging position, and the CT gantry 2 is set at the imaging portion of the subject P, for conformation imaging by the CT.

Step ST11 performed at the time of paracentesis and step ST12 performed for the confirmation imaging will be described in detail, referring to the flowchart shown in FIG. 8. In the description below, the processing included in step ST11 will be referred to as steps ST11-1 to ST11-9, and the processing included in step ST12 will be referred to as steps ST12-1 to ST12-3.

In step ST11-1, the angio console 6 generates an X-ray image of the paracentesis and displays it on the display 64.

In step ST11-2, the system control circuitry 66 determines whether or not predetermined conditions are met. If the predetermined conditions are met, the control proceeds to step ST11-3. If they are not met, the control proceeds to step ST11-4. The predetermined conditions mentioned here are conditions indicating the possibility that the paracentesis needle 8 might move out of the updated first interference determination area A1. For example, the predetermined conditions include a decrease of that length of the paracentesis needle 8 which is located inside the subject P.

In step ST11-3, the system control circuitry 66 initializes the first interference determination area A1 (which becomes narrow as a result of the repeated setting in step ST11-6), with a predetermined condition as a trigger.

In step ST11-4, the system control circuitry 66 determines whether or not the working angle is the vertical viewing angle. If the working angle is the vertical viewing angle, the control proceeds to step ST11-5. If it is not, the control proceeds to step ST11-7.

In step ST11-5, the system control circuitry 66 derives a projection amount of the paracentesis needle 8 from the subject P, based on the image of the paracentesis needle 8 included in the X-ray image. The image of the paracentesis needle 8 is located near the paracentesis portion 91 and the path 9, and is detected as an image of a black line substantially parallel to the path 9. If a plurality of candidates of the image of the paracentesis needle 8 are present, the operator may select one of them based on the operator's judgment. The system control circuitry 66 derives the length of the paracentesis needle 8 which is inside the subject P from the image of the paracentesis needle 8, and subtracts the derived length from the overall length of the paracentesis needle 8 set beforehand, thereby deriving a projection amount of the paracentesis needle 8 from the subject P. At the time, the system control circuitry 66 may read from the storage 65 the overall length of the paracentesis needle 8 which is set beforehand, and may use the read overall length for the subtraction. This modification example is applicable to each of the embodiments and modifications described below.

In step ST11-6, the system control circuitry 66 sets a first interference determination area A1 including the paracentesis needle 8 projecting from the subject P, based on the derived projection amount. Steps ST11-5 and ST11-6 (the derivation of a projection amount and the setting of a first interference determination area A1) may be automatically performed after the activation of the paracentesis assistance function, or may be performed with an operation by the operator as a trigger.

In steps ST11-7 and ST11-8, the system control circuitry 66 determines whether or not the working angle should be changed based on the switching operation is performed by the operator. If the result of determination is affirmative, the working angle is changed. If the working angle is not changed, the control proceeds to step ST11-9. The working angles are alternately switched during the paracentesis so that the state of the paracentesis needle 8 can be confirmed. At the vertical viewing angle, the position of the distal end of the paracentesis needle 8 and the direction of the paracentesis needle 8 can be confirmed. At the parallel viewing angle, the direction of the paracentesis needle 8 can be confirmed. When the working angles are switched, the system control circuitry 66 controls the holding device such that the movement of the imaging device 5 is restricted in each of the interference determination areas A1 and A2. When the movement of the imaging device 5 is restricted, the system control circuitry 66 may issue notification if the imaging device 5 enters each of the interference determination areas A1 and A2.

In step ST11-9, the control proceeds to different steps, depending upon whether or not the paracentesis ends. If the paracentesis has not yet ended, the control returns to step ST11-1, and the paracentesis is continued. If the paracentesis has ended, the control proceeds to step ST12-1.

In step ST12-1, the system control circuitry 66 starts auto-positioning in response to an operation by the operator.

When the imaging device 5 is retracted from the imaging position, the system control circuitry 66 controls the holding device in step ST12-2 such that the movement of the imaging device 5 is restricted in the second interference determination area A2 updated in step ST6 and in the first interference determination area A1 set in step ST11-6. When the CT gantry 2 is arranged at the imaging position, the system control circuitry 66 controls the movement of the CT gantry 2 and the couch top 7a such that the CT gantry 2 and the couch top 7a do not enter the first or second interference determination area A1 or A2. For example, if the CT gantry 2 is likely to collide with the couch top 7a or the like when it is moved toward the imaging position, the CT gantry 2 is temporarily stopped and the couch top 7a is moved in the vertical direction. Thereafter, the CT gantry 2 is moved and is arranged at the imaging position.

In step ST12-3, performed after the end of the auto-positioning, the imaging device 5 is retracted from the imaging position and the CT gantry 2 is set at the imaging portion of the subject P.

In the above-mentioned manner, step ST12 is ended.

Figure 7:
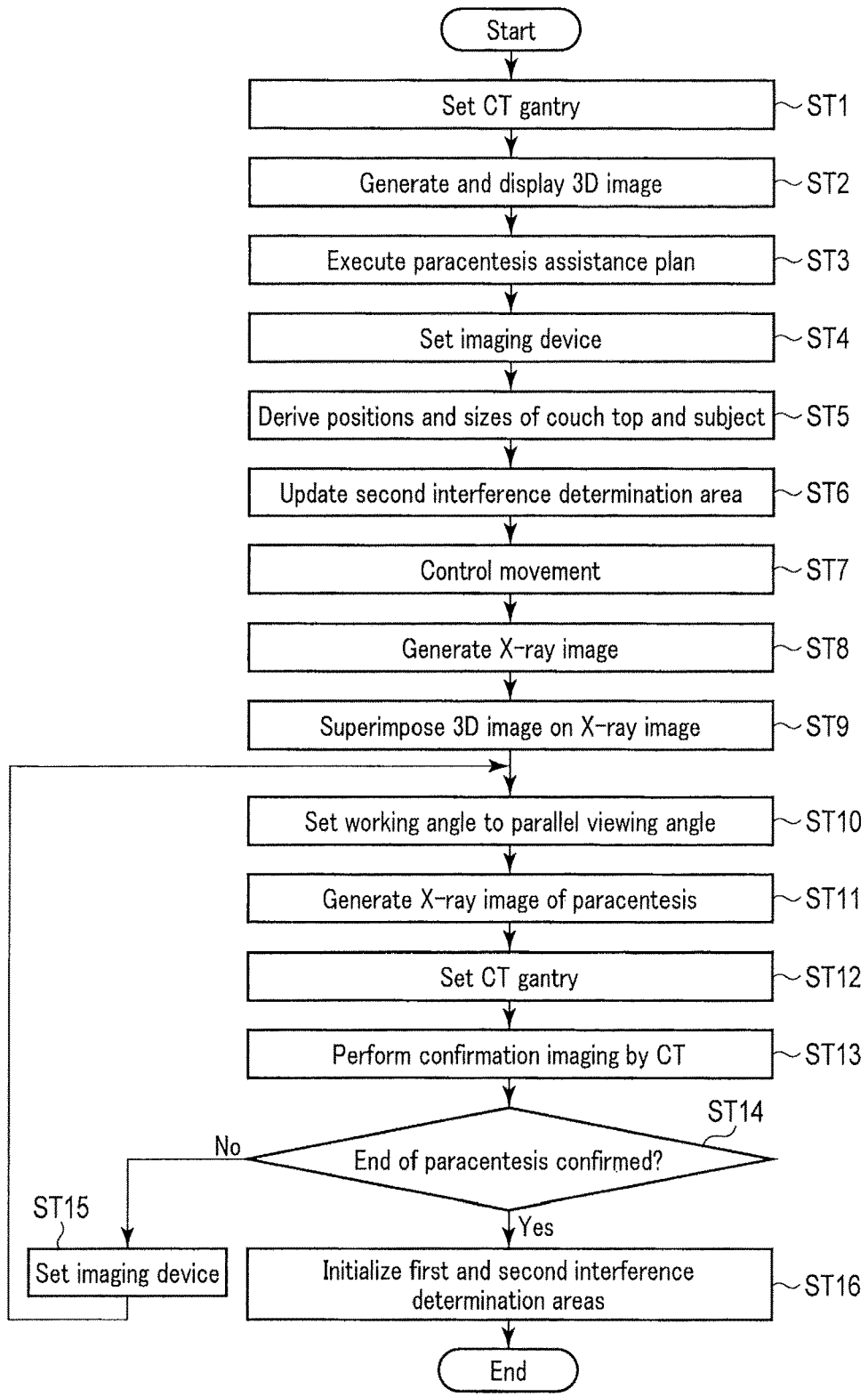
FIG. 7 is a flowchart illustrating an operation performed in the embodiment.
Figure 8:
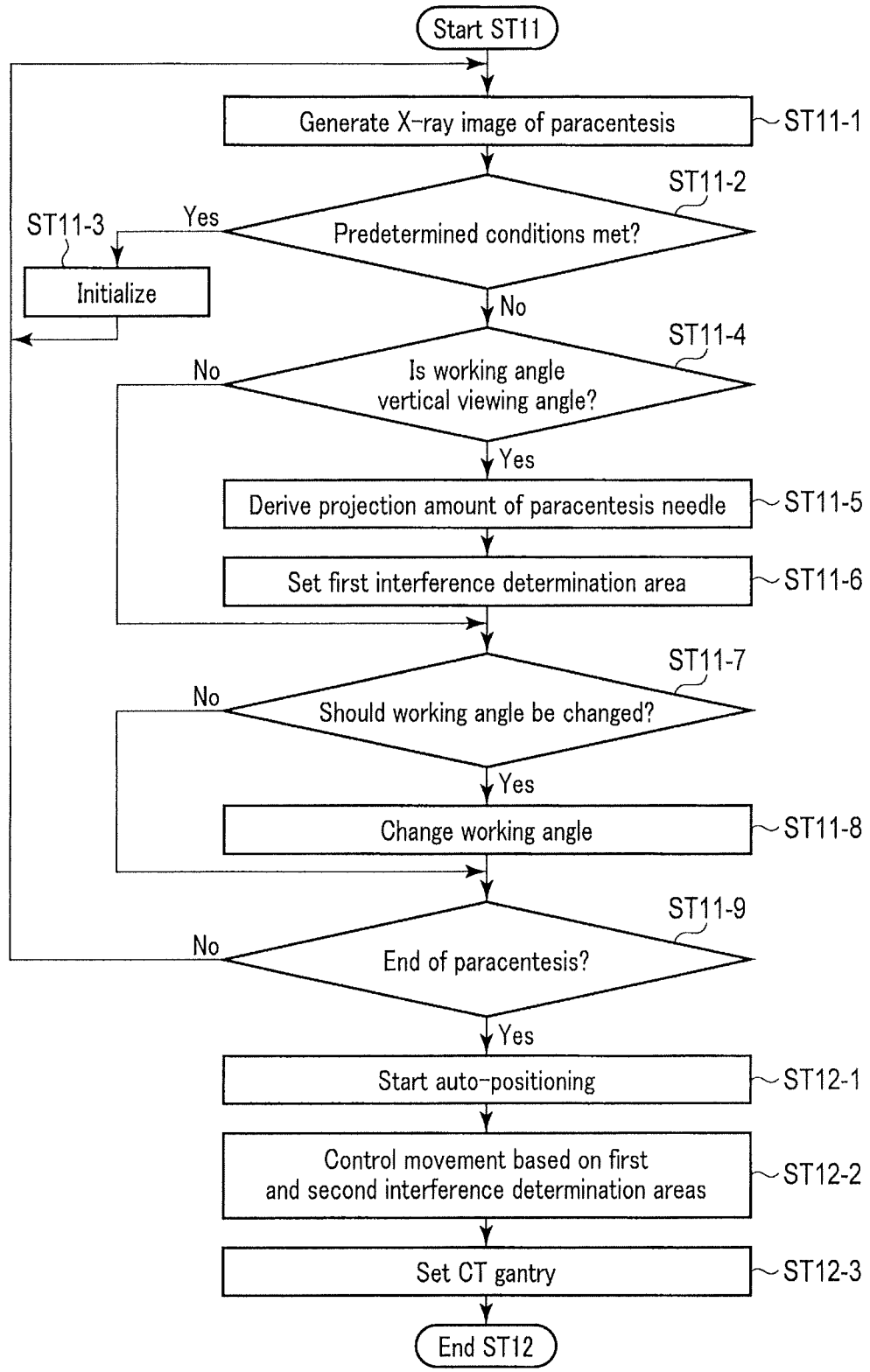
FIG. 8 is a flowchart illustrating an operation performed in the embodiment.

In step ST13, the CT apparatus performs confirmation imaging, as shown in FIG. 7.

In step ST14, the control proceeds to different steps, depending upon whether or not the end of the paracentesis is confirmed based on the confirmation imaging. If the end of the paracentesis is not confirmed, the control proceeds to step ST15, and the paracentesis is continued. If the end of the paracentesis is confirmed, the control proceeds to step ST16.

In step ST15, performed after the CT gantry 2 is retracted from the imaging position, the imaging device 5 is set at the position where it was before the execution of step ST12.

After the end of the paracentesis, a tissue piece of a tumor is taken or an ablation treatment is performed by means of the paracentesis needle 8. Thereafter, in step ST16, the first and second interference determination areas A1 and A2 are initialized. Subsequently, the paracentesis assistance function is ended.

As described above, according to the first embodiment, a first interference determination area including a device projecting from a subject is set based on an image of the device included in an X-ray image. In addition, the holding device is controlled such that the movement of the imaging device is restricted in the set first interference determination area.

Accordingly, the collision with the device projecting from the subject is prevented, and the labor and time in positioning can be alleviated. Furthermore, since an optimal interference determination area can be set during the medical procedure without additionally using a dedicated sensor, jig or the like, the safety can be ensured, and the efficiency of the medical procedure can be improved.

Controlling the holding device may include controlling the holding device in such a manner that the imaging device does not enter the first interference determination area. In this case, the collision with a device projecting from the subject can be prevented very reliably.

In addition, controlling the holding device may include controlling the holding device in such a manner that the moving speed of the imaging device is lower in the first interference determination area than in the areas other than the first interference determination area. In this case, the imaging device can be arranged close to the device, while simultaneously preventing the collision with the device projecting from the subject.

In addition, the use of the second interference determination area for protecting the couch top and the subject enables the X-ray generator and the X-ray detector to be arranged close to the couch top and the subject, respectively, so that an X-ray image of high quality can be taken. The use of the first interference determination area for protecting the device projecting from the subject prevents an object moving at the time of auto-positioning from colliding with the device and thus protects the device. To supplement the description, the distance between the X-ray generator and the X-ray detector with the subject in between should be as short as possible. Where this distance is short, an X-ray image is not blurred and has a good image quality. The second interference determination area and the first interference determination area are set as different areas. With this feature, the outer periphery of the second interference determination area and the body surface of the subject can be made so close to each other that the device projecting from the subject is viewed as if it projects from the second interference determination area. Accordingly, the X-ray detector can be arranged close to the body surface of the subject, and the image quality of an X-ray image can be improved. In addition, the device projecting from both the subject and the second interference determination area can be protected using the first interference determination area.

Accordingly, the image quality of an X-ray image can be improved, and, as mentioned above, the safety can be ensured and the efficiency of the medical procedure can be improved by setting an optimal interference determination area during the medical procedure. Furthermore, as mentioned above, the collision with the device projecting from the subject can be prevented during the auto-positioning, and the labor and time in positioning can be alleviated.

According to the first embodiment, a memory (storage 65) which stores the overall length of a device is employed. How the device projects from the subject P may be derived from the overall length of the device, and a first interference determination area may be set based on the derived projection amount. In this case, even if an image of the device included in an X-ray image shows only part of the device, the projection amount of the device from the subject P can be derived. To be specific, the length of the device inserted into the subject is derived from the image of the device, and the derived length is subtracted from the overall length of the device, thereby deriving a projection amount of the device. In this case, the confusion between an image of the device included in an X-ray image and a black-line image of an object other than the device can be avoided.

According to the first embodiment, the first interference determination area (which becomes narrow as a result of repeated setting) may be initialized, with predetermined condition as a trigger. For example, on the condition that the length of the device inserted into the subject decreases, the first interference determination area can be maximized (which is an initial setting size), and the device can be prevented from projecting from the first interference determination area, with the result that the safety can be ensured. The condition that the length of the device inserted into the subject decreases indicates that the length (projection amount) of the device projecting from the subject increases.

According to the first embodiment, the derivation of the projection amount may be started, with a predetermined operation by the operator as a trigger. In this case, the derivation of the projection amount may be started at a time desired by the operator.

According to the first embodiment, the projection amount may be derived in real time and the first interference determination area may be set in real time when the device is being advanced into the subject P. In this case, the first interference determination area can be set in accordance with how the device is advanced into the subject.

<Modification>

Next, a modification of the first embodiment will be described.

According to the first embodiment, the first interference determination area A1 is set at the time of paracentesis. According to the modification of the first embodiment, the first interference determination area A1 is set in response to the start of the movement of the arm during the auto-positioning.

To be specific, when the entire C arm 54 including the X-ray tube 52 and the X-ray detector 53 is moved to the predetermined retracted position, the system control circuitry 66 uses the start of the movement as a trigger, and starts the derivation of the projection amount and sets the first interference determination area A1, based on the derived projection amount.

The other configurations are similar to those of the first embodiment.

Figure 9:
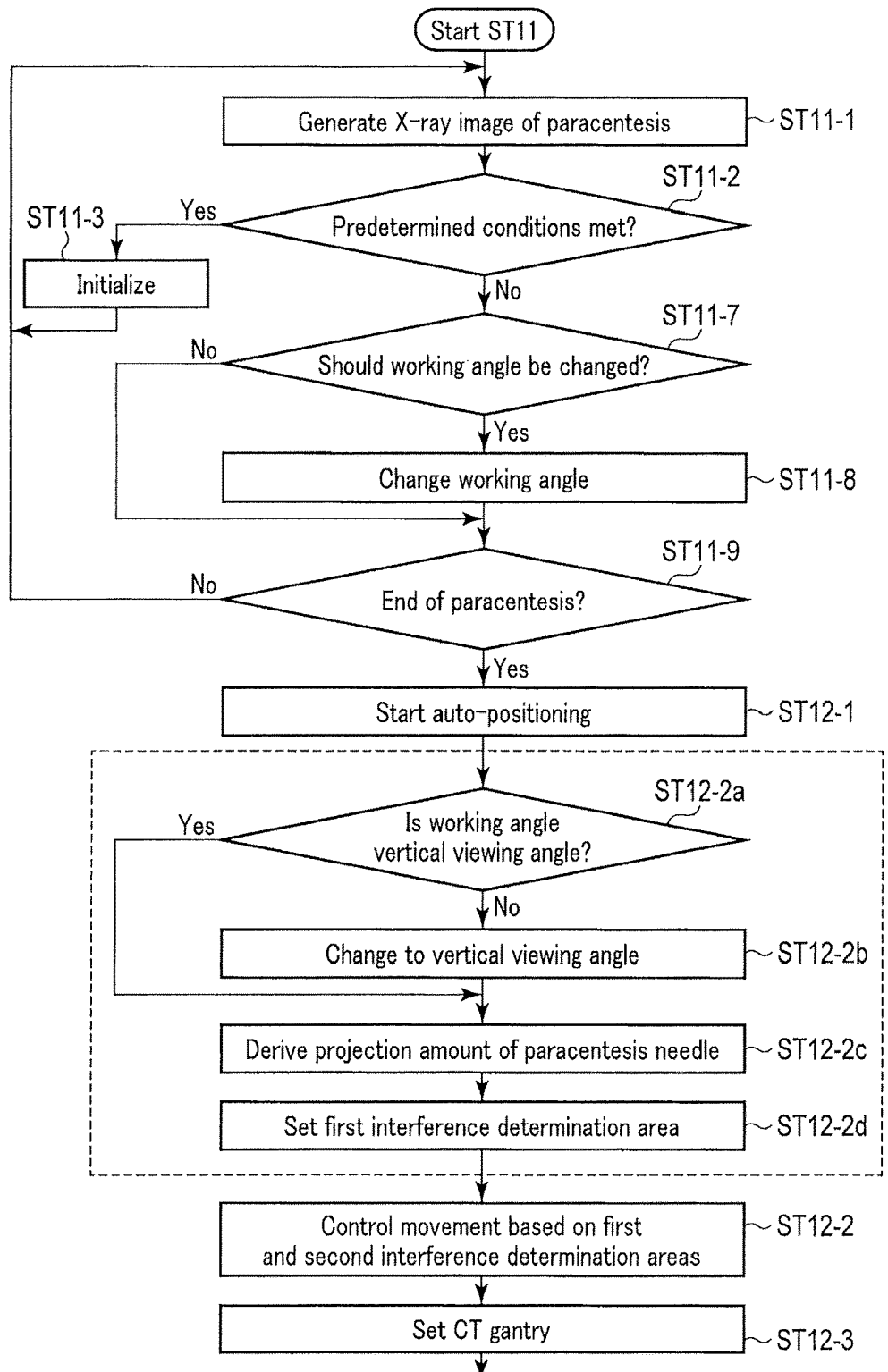
FIG. 9 is a flowchart illustrating an operation performed in a modification of the embodiment.

An operation of the modification having the above configurations will be described with reference to the flowchart of FIG. 9. On the whole, the modification performs the same steps ST1 to ST16 as shown in FIG. 7. However, the modification differs from the first embodiment in terms of the details of steps ST11 and ST12, as shown in FIG. 9. In the description below, therefore, reference will be made only to the details of steps ST11 and ST12.

In step ST11, steps ST11-1 to ST11-3 and steps ST11-7 to ST11-9 mentioned above are executed. That is, according to the modification, steps ST11-4 to ST11-6 (the confirmation of the vertical viewing angle, the derivation of the projection amount of the paracentesis needle, and the setting of the first interference determination area A1) are not executed.

Subsequently, in step ST12, steps ST12-2a to ST12-2d are executed between step ST12-1 and step ST12-2 which were mentioned above. That is, according to the modification, when the auto-positioning of step ST12-1 is started, the confirmation of the vertical viewing angle, the derivation of the projection amount of the paracentesis needle, and the setting of the first interference determination area A1 are executed.

To be specific, in steps ST12-2a and ST12-2b, the system control circuitry 66 determines whether or not the working angle is a vertical viewing angle, and if the working angle is not, changes it to the vertical viewing angle. If the working angle is the vertical viewing angle, the control proceeds to step ST12-2c. If the inspection routine or the like determines that the working angle at the start time of the auto-positioning is the vertical viewing angle, then steps 12-2a and ST12-2b are not required.

In step ST12-2c, the system control circuitry 66 derives a projection amount of the paracentesis needle 8 from the subject P, based on the image of the paracentesis needle 8 included in the X-ray image. At the time, the start of the movement of the entire C arm 54 including the X-ray tube 52 and the X-ray detector 53 to the predetermined retracted position is used as a trigger.

In step ST12-2d, the system control circuitry 66 sets a first interference determination area A1 including the paracentesis needle 8 projecting from the subject P, based on the derived projection amount.

Subsequently, steps ST12-2 and ST12-3 are performed in a similar way to that mentioned above.

As described above, according to the modification of the first embodiment, the derivation of the projection amount is started, using the start of the movement of the entire holding device including both the X-ray generator and the X-ray detector to the predetermined retracted position as a trigger. In addition to the advantages of the first embodiment, the modification is advantageous in that the processing of deriving a projection amount and the processing of setting a first interference determination area can be executed simultaneously with the start of the auto-positioning.

Second Embodiment

FIG. 10 is a schematic diagram showing a configuration of an X-ray diagnostic apparatus according to a second embodiment. In FIG. 10, the same reference symbols as used in FIG. 3A denote substantially the same elements, and a detailed description of such elements will be omitted. A description will be given mainly of the differences.

The second embodiment is a modification of the first embodiment. The X-ray diagnostic apparatus is configured such that the CT gantry 2 and the CT console 3 of the medical image diagnostic system shown in FIG. 3A are omitted and an imaging device 5 and an angio console 6 are added, as shown in FIG. 10.

The imaging device 5 and the angio console 6 are similar to those mentioned in connection with the first embodiment. Since the CT gantry 2 is omitted, the system control circuitry 66 of the angio console 6 does not possess all of the above-mentioned functions. That is, the control function used when a modality (e.g., the CT gantry 2) is arranged at an imaging position is omitted. When a modality is arranged at an imaging position, the system control circuitry 66 does not control the movement of the modality and the couch top 7a such that the modality and the couch top 7a do not enter the first or second interference determination area A1 or A2. Since the modality is omitted, there is no fear that the couch top 7a will collide with a modality. Therefore, the couch top 7a does not have to be movable in the vertical direction. As for the control function of controlling the movement of the imaging device 5, the system control circuitry has this function, as described above. As described above, the period in which the control function performs control is not limited to the period in which the auto-positioning is executed. Likewise, in order to prevent the collision with a device projecting from a subject, the control function may perform control such that entry to at least the first interference determination area A1 is prevented, not entry to both the first and second interference determination areas A1 and A2.

Figure 12:
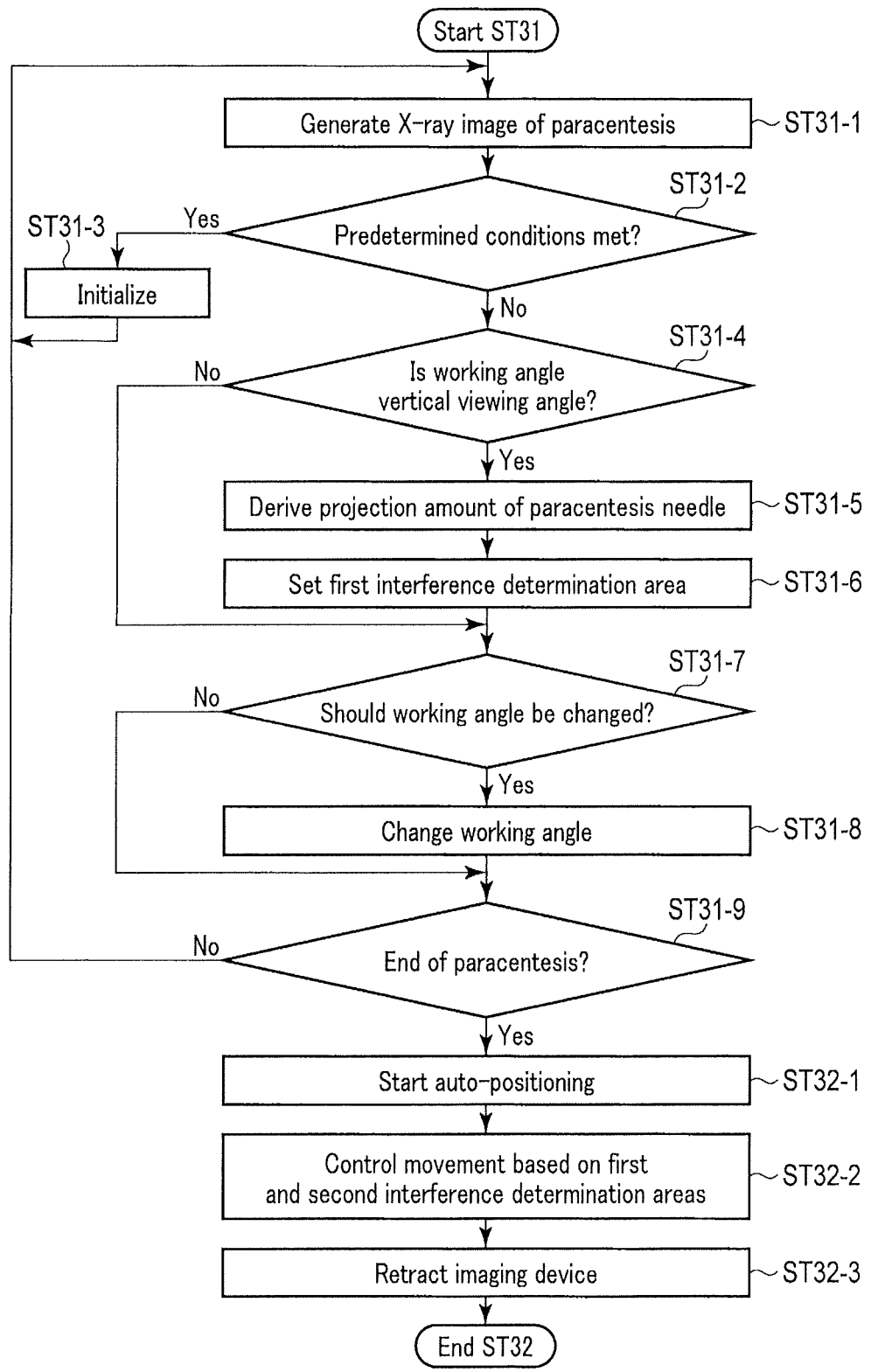
FIG. 12 is a flowchart illustrating an operation performed in the embodiment.
Figure 13:
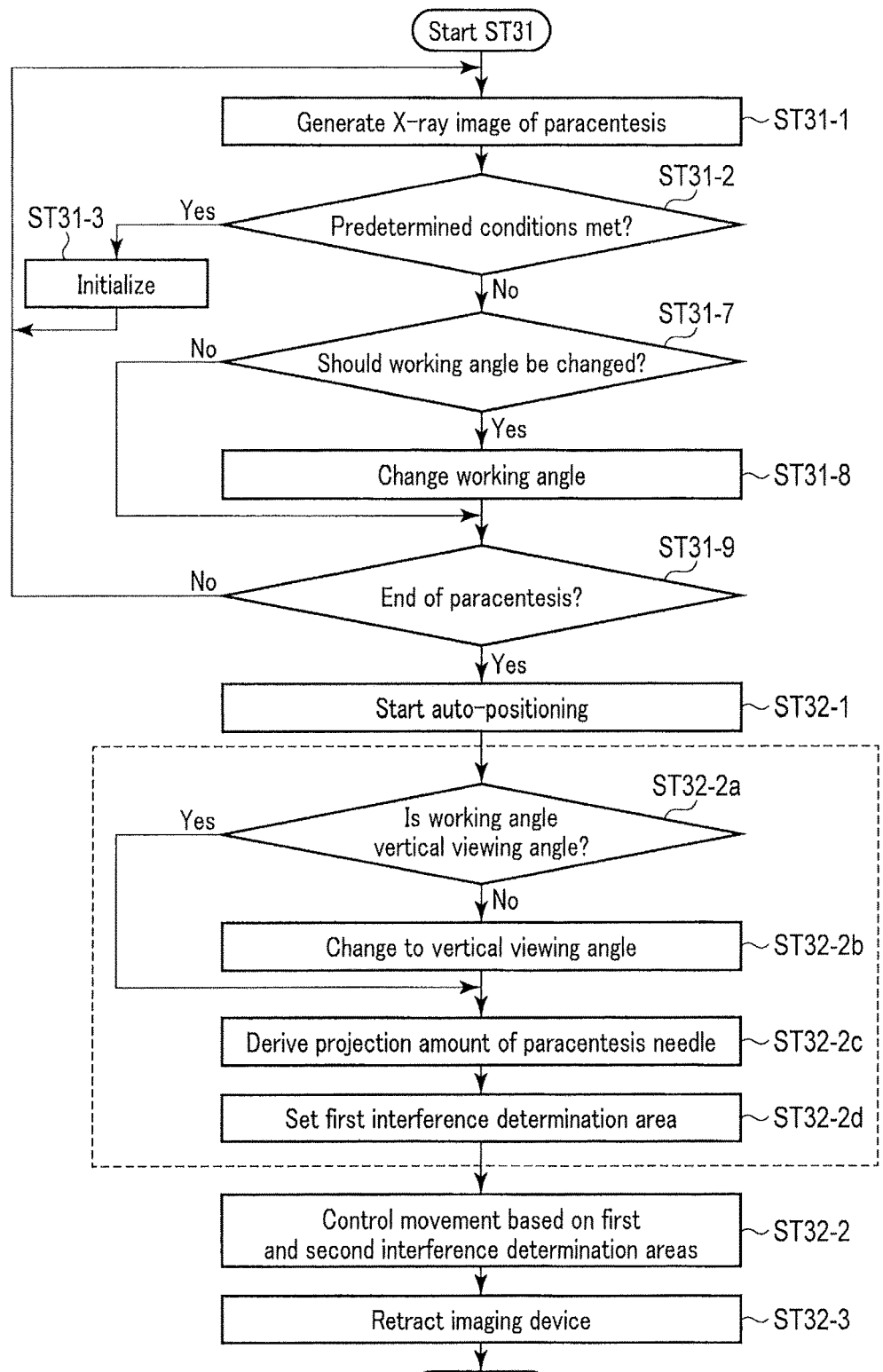
FIG. 13 is a flowchart illustrating an operation performed in a modification of the embodiment.

An operation of the X-ray diagnostic apparatus having the above configurations will be described with reference to the flowchart of FIG. 11 to FIG. 13.

In step ST21, a CT apparatus (not shown) performs CT imaging beforehand, and a 3D image of a subject P is obtained thereby. This 3D image is transferred from the CT apparatus to the angio console 6. The 3D image of the subject P is stored in the storage 65.

In step ST22, the system control circuitry 66 of the angio console 6 displays the 3D image stored in the storage 65 on the display 64.

In step ST23, the system control circuitry 66 executes a paracentesis assistance plan, as in step ST3.

In step ST24, the system control circuitry 66 of the angio console 6 sets the imaging device 5 at a position close to an imaging position of the subject P lying on the couch top 7a.

The processing in step ST25 to step ST31 is performed in the same way as the above-mentioned processing in step ST5 to step ST11.

In step ST32, the imaging device 5 is retracted from the imaging position to perform a medical procedure or treatment.

Step ST31 performed at the time of the paracentesis and step ST32 performed at the time of the angio retraction will be described in detail, referring to the flowchart shown in FIG. 12. In the description below, the processing included in step ST31 will be described as steps ST31-1 to ST31-9, and the processing included in step ST32 will be described as steps ST32-1 to ST32-3.

The processing in step ST31-1 to ST31-9 and the processing in ST32-1 are performed in the same way as the above-mentioned processing in step ST11-1 to ST11-9 and processing in ST12-1.

In step ST32-2, when the imaging device 5 is retracted from the imaging position, the system control circuitry 66 controls the movement of the imaging device 5 such that the imaging device 5 does not enter the first or second interference determination area A1 or A2 updated in steps ST31-6 and ST26.

In step ST32-3, the imaging device 5 is retracted from the imaging position after the end of auto-positioning.

In the above-mentioned manner, step ST32 is ended.

Figure 11:
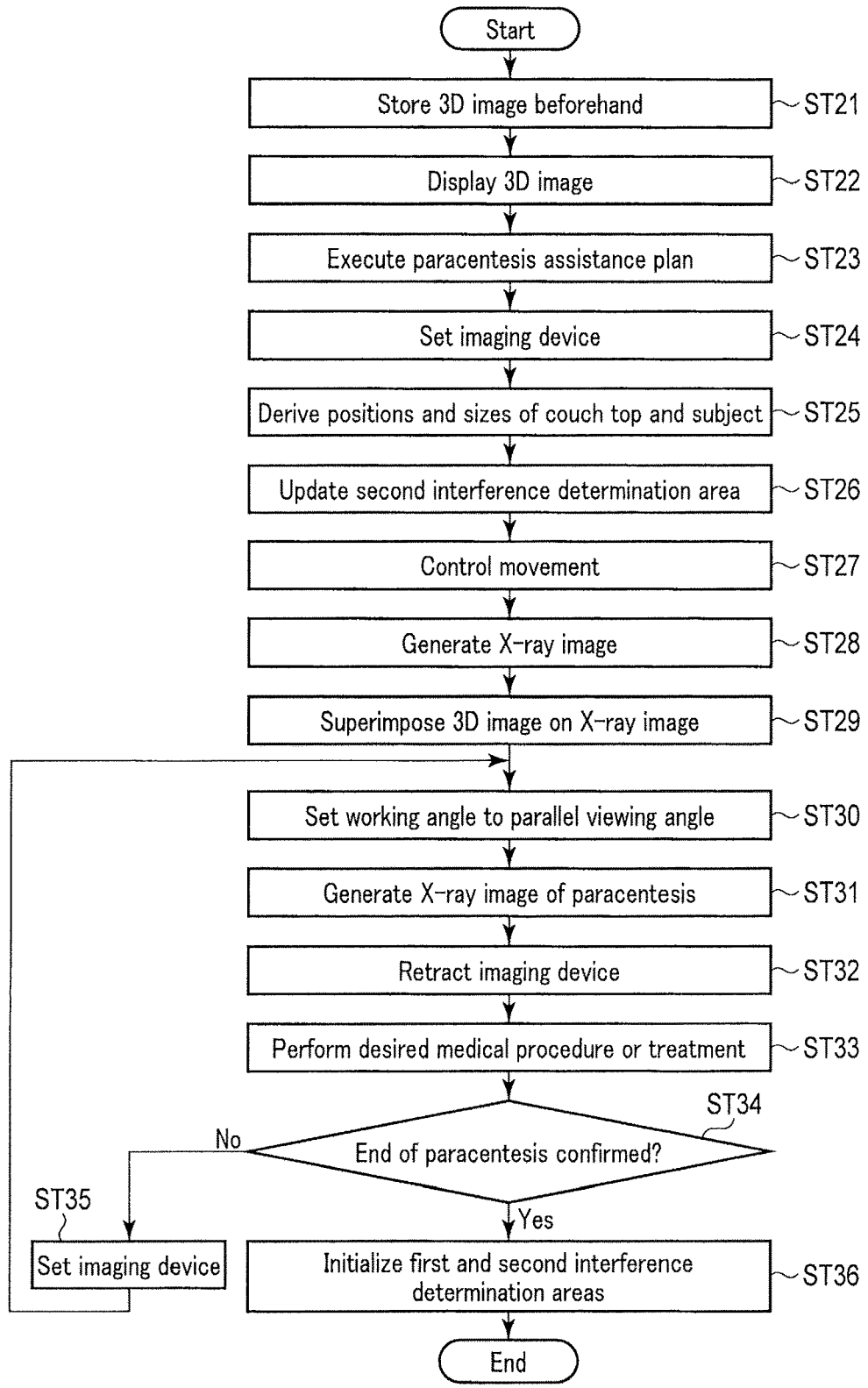
FIG. 11 is a flowchart illustrating an operation performed in the embodiment.

In step ST33, the surgeon performs a desired medical procedure or treatment for the subject P, with the imaging device 5 retracted, as shown in FIG. 11.

In step ST34, which follows the medical procedure or treatment in step ST33, the control proceeds to different steps, depending upon whether or not the end of the paracentesis is confirmed. If the end of the paracentesis is not confirmed, the control proceeds to step ST35, and the paracentesis is continued. If the end of the paracentesis is confirmed, the control proceeds to step ST36.

In step ST35, the imaging device 5 is set at the position where it was before the execution of step ST32.

The processing in step ST36 is performed in the same way as the above-mentioned processing in step ST16. As a result, the first and second interference determination areas A1 and A2 are initialized, and the paracentesis assistance function is ended.

As described above, according to the second embodiment, such a CT apparatus as employed in the first embodiment (which comprises the X-ray diagnostic apparatus and the CT apparatus) is omitted, and the apparatus of the second embodiment is limited to the X-ray diagnostic apparatus. Despite this, however, the advantages are similar to those of the first embodiment.

That is, according to the second embodiment, the collision with the device projecting from the subject can be prevented, and the labor and time in positioning can be alleviated. Furthermore, since an optimal interference determination area can be set during the medical procedure without additionally using a dedicated sensor, jig or the like, the safety can be ensured, and the efficiency of the medical procedure can be improved.

Likewise, when the length of the device inserted into the subject is derived from the image of the device, and the derived length is subtracted from the overall length of the device to derive a projection amount of the device, the confusion between an image of the device included in an X-ray image and a black-line image of an object other than the device can be avoided.

Likewise, when the first interference determination area (which becomes narrow as a result of the repeated setting) is initialized, with a predetermined condition as a trigger, the device does not project from the first interference determination area even if the length of the device inside the subject decreases. As a result, the safety is improved.

Likewise, when the derivation of the projection amount is started, with a predetermined operation as a trigger, the derivation of the projection amount can be started at a time desired by the operator.

Likewise, where the projection amount is derived in real time and the first interference determination area is set in real time when the device is being advanced into the subject P, the first interference determination area can be set in accordance with how the device is advanced.

<Modification>

Next, a modification of the second embodiment will be described.

According to the second embodiment, the first interference determination area A1 is set at the time of paracentesis. According to the modification of the second embodiment, the first interference determination area A1 is set after the start of auto-positioning. In other words, the modification of the second embodiment is obtained by applying the modification of the first embodiment to the second embodiment.

When the entire C arm 54 including both the X-ray tube 52 and the X-ray detector 53 is moved to the predetermined retracted position, the system control circuitry 66 uses the start of this movement as a trigger to start the derivation of a projection amount and sets the first interference determination area A1, based on the derived projection amount.

The other configurations are similar to those of the second embodiment.

An operation of the modification having the above configurations will be described with reference to the flowchart of FIG. 13. On the whole, the modification performs the same steps ST21 to ST36 as shown in FIG. 11. The modification differs from the second embodiment in terms of the details of steps ST31 and ST32, as shown in FIG. 13. In the description below, therefore, reference will be made only to the details of steps ST31 and ST32.

In step ST31, steps ST31-1 to ST31-3 and steps ST31-7 to ST31-9 mentioned above are executed. That is, according to the modification, steps ST31-4 to ST31-6 (the confirmation of the vertical viewing angle, the derivation of the projection amount of the paracentesis needle, and the setting of the first interference determination area A1) are not executed.

Subsequently, in step ST32, steps ST32-2a to ST32-2d are executed between step ST32-1 and step ST32-2 which were mentioned above. That is, according to the modification, when the auto-positioning of step ST32-1 is started, the confirmation of the vertical viewing angle, the derivation of the projection amount of the paracentesis needle, and the setting of the first interference determination area A1 are executed.

To be specific, in steps ST32-2a and ST32-2b, the system control circuitry 66 determines whether or not the working angle is a vertical viewing angle, and if the working angle is not, changes it to the vertical viewing angle. If the working angle is the vertical viewing angle, the control proceeds to step ST32-2c.

In step ST32-2c, the system control circuitry 66 derives a projection amount of the paracentesis needle 8 from the subject P, based on the image of the paracentesis needle 8 included in the X-ray image.

In step ST32-2d, the system control circuitry 66 sets a first interference determination area A1 including the paracentesis needle 8 projecting from the subject P, based on the derived projection amount.

Subsequently, steps S32-2 and ST32-3 are executed in the same manner as mentioned above.

As described above, according to the modification of the second embodiment, the derivation of a projection amount is started, using the start of the movement of the entire holding device including both the X-ray generator and the X-ray detector to the predetermined retracted position as a trigger. In addition to the advantages of the second embodiment, the modification is advantageous in that the processing of deriving a projection amount and the processing of setting a first interference determination area can be executed simultaneously with the start of the auto-positioning.

The term "processor" used in the above descriptions is, for example, a central processing unit (CPU) or a graphics processing unit (GPU), or includes application-specific integrated circuitry (ASIC), a programmable logic device (such as a simple programmable logic device (SPLD)), a complex programmable logic device (CPLD), a field programmable gate array (FPGA) or the like. The processor reads the programs stored in a storage and executes them to realize the respective functions. The programs may be incorporated in the circuitry of the processor, instead of storing them in the storage. In this case, the processor reads the programs incorporated in its circuitry and executes them to realize the respective functions. The processors described in connection with the embodiments are not limited to single-circuit processors. A plurality of independent processors may be combined and integrated as one processor having multiple functions. Furthermore, a plurality of structural elements shown in FIG. 3A and FIG. 10 may be integrated as one processor having multiple functions.

The X-ray tube 52 described in connection with each embodiment is an example of the X-ray generator recited in the claims. The C arm 54, the holding unit 54a and the support arm 54b described in connection with each embodiment are examples of the holding device recited in the claims. The processing circuitry 67 (the image generation circuitry 61 and the system control circuitry 66) described in connection with each embodiment is an example of the processing circuitry recited in the claims. The image of the paracentesis needle 8 described in connection with each embodiment is an example of the image of the device recited in the claims or an example of the image of the needle recited in the claims. The paracentesis needle 8 described in connection with each embodiment is an example of the device or needle recited in the claims.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising:
a couch including a couch top on which a subject lies;
an imaging unit including an X-ray generator configured to radiate X-rays to the subject, an X-ray detector configured to detect X-rays transmitted through the subject, and a holding device which movably holds the X-ray generator and the X-ray detector; and
processing circuitry configured to
generate an X-ray image of the subject, based on an output of the X-ray detector,
set a first interference determination area including a device projecting from the subject, based on an image of the device included in the X-ray image, and
control the holding device such that movement of the imaging unit is restricted in the first interference determination area.

2. The X-ray diagnostic apparatus according to claim 1, wherein the processing circuitry is further configured to control the holding device such that the imaging unit is prevented from entering the first interference determination area.

3. The X-ray diagnostic apparatus according to claim 1, wherein the processing circuitry is further configured to control the holding device such that a moving speed of the imaging unit is lower in the first interference determination area than in areas other than the first interference determination area.

4. The X-ray diagnostic apparatus according to claim 1, wherein the processing circuitry is further configured to derive a projection amount of the device from the subject and set the first interference determination area, based on the derived projection amount.

5. The X-ray diagnostic apparatus according to claim 4, wherein the processing circuitry is further configured to derive the projection amount by deriving a length of the device inserted into the subject, based on an image of the device, and subtracting the derived length from an overall length of the device.

6. The X-ray diagnostic apparatus according to claim 5, further comprising:
a memory configured to store the overall length of the device beforehand,
wherein the processing circuitry is further configured to read the overall length of the device from the memory and use the overall length in subtraction.

7. The X-ray diagnostic apparatus according to claim 4, wherein the processing circuitry is further configured to start derivation of the projection amount, with a predetermined operation by an operator as a trigger.

8. The X-ray diagnostic apparatus according to claim 4, wherein the processing circuitry is further configured to start derivation of the projection amount, using as a trigger start of the movement of the entire holding device including both the X-ray generator and the X-ray detector to a predetermined retracted position.

9. The X-ray diagnostic apparatus according to claim 4, wherein the processing circuitry is further configured to derive the projection amount in real time and set the first interference determination area in real time, when the device is being advanced into the subject.

10. The X-ray diagnostic apparatus according to claim 1, wherein the processing circuitry is further configured to initialize the first interference determination area, which becomes narrow as a result of repeated setting, with a predetermined condition as a trigger.

11. The X-ray diagnostic apparatus according to claim 1, wherein the device is a needle, and the image of the device is an image of the needle.

12. The X-ray diagnostic apparatus according to claim 1, wherein the processing circuitry is further configured to update a second interference determination area including both the couch top and the subject, based on a geometric imaging condition of the X-ray image, and control the movement of the imaging unit while simultaneously preventing the imaging unit from entering the updated second interference determination area and the first interference determination area.

13. The medical image diagnostic apparatus according to claim 1, wherein the processing circuitry is further configured to control the movement when the imaging unit is retracted from an imaging position.

14. A medical image diagnostic system comprising:
a couch which holds a couch top on which a subject lies, such that the couch top is movable in a vertical direction;
an imaging unit including an X-ray generator configured to radiate X-rays to the subject, an X-ray detector configured to detect X-rays transmitted through the subject, and a holding device which movably holds the X-ray generator and the X-ray detector;
a modality used alternately with the imaging unit and moved closer to or away from a subject; and
processing circuitry configured to
generate an X-ray image of the subject, based on an output of the X-ray detector,
set a first interference determination area including a device projecting from the subject, based on an image of the device included in the X-ray image, and
control the holding device such that movement of the imaging unit is restricted in the first interference determination area.

15. The medical image diagnosis system according to claim 14, wherein the processing circuitry is further configured to issue a notification indicating that the imaging unit enters the first interference determination area.

16. A control method for controlling a medical image diagnostic apparatus that comprises:
- a couch including a couch top on which a subject lies; and
- an imaging unit including an X-ray generator configured to radiate X-rays to the subject, an X-ray detector configured to detect X-rays transmitted through the subject, and a holding device which movably holds the X-ray generator and the X-ray detector;

the control method comprising:
- generating an X-ray image of the subject, based on an output of the X-ray detector;
- setting a first interference determination area including a device projecting from the subject, based on an image of the device included in the X-ray image; and
- controlling the holding device such that movement of the imaging unit is restricted in the first interference determination area.

17. The control method according to claim 16, wherein controlling the holding device includes controlling the holding device such that the imaging unit is prevented from entering the first interference determination area.

18. The control method according to claim 16, wherein controlling the holding device includes controlling the holding device such that a moving speed of the imaging unit is lower in the first interference determination area than in areas other than the first interference determination area.

19. The control method according to claim 16, wherein setting the first interference determination area includes deriving a projection amount of the device from the subject and setting the first interference determination area, based on the derived projection amount.

20. The control method according to claim 19, wherein setting the first interference determination area includes deriving a length of the device inserted into the subject, based on an image of the device, and subtracting a derived length from an overall length of the device.

* * * * *